(12) United States Patent
Cantwell et al.

(10) Patent No.: US 11,672,487 B2
(45) Date of Patent: Jun. 13, 2023

(54) PLEDGET STIMULATION AND RECORDING ELECTRODE ASSEMBLIES

(71) Applicant: Medtronic Xomed, Inc., Jacksonville, FL (US)

(72) Inventors: Matthew L. Cantwell, Orange Circle, FL (US); David C. Hacker, Jacksonville, FL (US); John R. Prisco, Jacksonville, FL (US); Anirudhan Narasimhan, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 1158 days.

(21) Appl. No.: 16/152,624

(22) Filed: Oct. 5, 2018

(65) Prior Publication Data

US 2019/0104995 A1 Apr. 11, 2019

Related U.S. Application Data

(60) Provisional application No. 62/568,841, filed on Oct. 6, 2017.

(51) Int. Cl.
*A61B 5/00* (2006.01)
*A61N 1/05* (2006.01)
(Continued)

(52) U.S. Cl.
CPC .............. *A61B 5/6879* (2013.01); *A61B 5/24* (2021.01); *A61B 5/296* (2021.01); *A61B 5/407* (2013.01);
(Continued)

(58) Field of Classification Search
None
See application file for complete search history.

(56) References Cited

U.S. PATENT DOCUMENTS 2,660,175 A * 11/1953 Thrasher ................ A61B 5/252
248/362
2,714,196 A * 7/1955 Melehan ............ G01R 1/06788
439/425
(Continued)

FOREIGN PATENT DOCUMENTS

CN 1413240 A 4/2003
CN 105007851 A 10/2015
(Continued)

OTHER PUBLICATIONS

PCT Partial Search Report dated Feb. 21, 2019 for PCT/US2018/065326 (14 pages).
(Continued)

*Primary Examiner* — Carl H Layno
*Assistant Examiner* — Manolis Pahakis
(74) *Attorney, Agent, or Firm* — Harness, Dickey & Pierce, P.L.C.

(57) ABSTRACT

Aspects of the disclosure relate to pledget stimulation/recording electrode assemblies that are particularly useful for automatic periodic stimulation. Embodiments are compatible with nerve monitoring systems to provide continuous stimulation of a nerve during surgery. Disclosed embodiments include an electrode assembly having one or more electrodes rotatably supported by and positioned within a pledget substrate. The flexible pledget substrate conforms and fixates to bioelectric tissue to secure the electrode assembly in position, wrapped around the target tissue. In some embodiments, the pledget substrate includes two bodies, each including at least one electrode, the two bodies being selectively separable so that the bodies can be repositioned with respect to one another. The electrode assembly further includes a lead wire assembly including at least one insulating jacket positioned around a wire core. Optionally, (Continued)

the electrode assembly includes an insulating cup interconnecting the electrode and the insulating jacket.

19 Claims, 16 Drawing Sheets

(51) Int. Cl.
    *A61B 5/24*     (2021.01)
    *A61B 5/296*     (2021.01)
    *A61N 1/04*     (2006.01)
    *A61N 1/36*     (2006.01)

(52) U.S. Cl.
    CPC .......... *A61B 5/4064* (2013.01); *A61B 5/6838* (2013.01); *A61B 5/6847* (2013.01); *A61B 5/6877* (2013.01); *A61B 5/6882* (2013.01); *A61N 1/0428* (2013.01); *A61N 1/0551* (2013.01); *A61N 1/0553* (2013.01); *A61N 1/0558* (2013.01); *A61N 1/3605* (2013.01); *A61B 5/6848* (2013.01); *A61B 2505/05* (2013.01); *A61B 2560/0475* (2013.01)

(56) References Cited

U.S. PATENT DOCUMENTS

| | | | | |
|---|---|---|---|---|
| 2,916,719 | A * | 12/1959 | Toms | H01J 5/50 439/182 |
| 3,072,877 | A * | 1/1963 | Landwehr | H01R 11/22 439/482 |
| 3,085,577 | A * | 4/1963 | Berman | H01R 13/6277 600/394 |
| 3,295,515 | A * | 1/1967 | Kahn | A61B 5/25 600/397 |
| 3,420,223 | A * | 1/1969 | Day | A61B 5/25 600/397 |
| 3,498,291 | A * | 3/1970 | Bunn | A61B 5/25 600/372 |
| 3,574,305 | A * | 4/1971 | Muhl | A61B 5/25 252/514 |
| 3,581,736 | A * | 6/1971 | Zenkich | A61B 5/25 600/394 |
| 3,599,629 | A * | 8/1971 | Gordy | A61B 5/324 600/392 |
| 3,651,547 | A * | 3/1972 | Ishizaki | A44B 17/0011 24/676 |
| 3,740,703 | A * | 6/1973 | Sessions | H01R 11/22 439/829 |
| 3,750,094 | A * | 7/1973 | Zenkich | A61B 5/274 600/394 |
| 3,830,229 | A * | 8/1974 | Johnson | A61B 5/25 600/397 |
| 3,868,165 | A * | 2/1975 | Gonser | H01R 11/24 439/410 |
| 3,882,853 | A * | 5/1975 | Gofman | A61B 5/274 600/397 |
| 3,890,420 | A * | 6/1975 | Neward | A61B 5/288 264/261 |
| 3,946,730 | A * | 3/1976 | Monter | A61B 5/25 600/397 |
| 3,993,049 | A * | 11/1976 | Kater | A61B 5/282 600/397 |
| 3,998,215 | A * | 12/1976 | Anderson | A61B 5/25 600/397 |
| 4,040,697 | A | 8/1977 | Ramsay et al. | |
| 4,066,078 | A * | 1/1978 | Berg | A61N 1/0492 600/397 |
| 4,080,961 | A | 3/1978 | Eaton | |
| 4,090,752 | A * | 5/1978 | Long | G09B 23/288 600/397 |
| 4,112,941 | A * | 9/1978 | Larimore | A61B 5/274 439/153 |
| 4,126,126 | A * | 11/1978 | Bare | A61B 5/25 600/397 |
| 4,177,818 | A | 12/1979 | De Pedro | |
| 4,178,052 | A | 12/1979 | Ekbom et al. | |
| 4,207,904 | A * | 6/1980 | Greene | A61N 1/0492 607/152 |
| 4,254,764 | A | 3/1981 | Neward | |
| 4,274,420 | A * | 6/1981 | Hymes | A61B 5/259 600/397 |
| 4,303,293 | A | 12/1981 | Grunwald | |
| 4,327,737 | A * | 5/1982 | Szpur | A61B 5/25 600/394 |
| 4,331,153 | A * | 5/1982 | Healy | A61B 5/25 600/397 |
| 4,332,257 | A * | 6/1982 | Ayer | A61B 5/274 600/391 |
| 4,385,793 | A | 5/1983 | Koford et al. | |
| 4,466,441 | A * | 8/1984 | Skubitz | A61N 1/3752 607/115 |
| 4,490,005 | A * | 12/1984 | Hovey | H01R 4/26 600/394 |
| 4,515,162 | A * | 5/1985 | Yamamoto | A61B 5/259 600/397 |
| 4,522,211 | A * | 6/1985 | Bare | A61B 5/259 600/397 |
| 4,554,924 | A * | 11/1985 | Engel | A61N 1/0492 600/397 |
| 4,649,923 | A | 3/1987 | Hoffman | |
| 4,653,501 | A * | 3/1987 | Cartmell | A61B 5/259 600/397 |
| 4,706,680 | A * | 11/1987 | Keusch | A61B 5/274 600/397 |
| 4,757,817 | A * | 7/1988 | Healy | A61B 5/274 600/394 |
| 4,777,954 | A | 10/1988 | Keusch et al. | |
| 4,827,939 | A | 5/1989 | Cartmell et al. | |
| 4,936,306 | A * | 6/1990 | Doty | A61B 5/377 600/382 |
| 4,938,231 | A * | 7/1990 | Milijasevic | A61N 1/0587 607/129 |
| 4,979,517 | A * | 12/1990 | Grossman | A61N 1/0492 607/153 |
| 5,078,138 | A * | 1/1992 | Strand | A61B 5/259 600/372 |
| 5,123,413 | A * | 6/1992 | Hasegawa | A61N 1/32 607/67 |
| 5,197,471 | A * | 3/1993 | Otero | A61B 5/274 600/394 |
| 5,232,383 | A * | 8/1993 | Barnick | A61N 1/048 600/394 |
| 5,326,272 | A * | 7/1994 | Harhen | H01R 11/11 600/394 |
| 5,375,594 | A | 12/1994 | Cueva | |
| 5,402,780 | A * | 4/1995 | Faasse, Jr. | A61B 5/25 600/397 |
| 5,406,945 | A * | 4/1995 | Riazzi | A61B 5/25 600/394 |
| 5,421,748 | A | 6/1995 | Mouissie | |
| 5,431,166 | A * | 7/1995 | Macur | A61N 1/048 607/152 |
| 5,464,387 | A * | 11/1995 | Haak | A61N 1/0448 604/20 |
| 5,560,357 | A * | 10/1996 | Faupel | A61B 5/25 607/901 |
| 5,566,672 | A * | 10/1996 | Faasse, Jr. | A61N 1/0492 607/152 |
| 5,611,339 | A * | 3/1997 | Okabe | A61B 5/25 600/372 |
| 5,628,729 | A * | 5/1997 | Okabe | A61N 1/30 604/20 |
| 5,897,406 | A * | 4/1999 | Benes | H01R 11/22 439/859 |
| 5,928,142 | A * | 7/1999 | Cartmell | A61B 5/274 607/152 |
| 5,931,861 | A | 8/1999 | Werner et al. | |
| 6,122,554 | A | 9/2000 | Coral et al. | |

(56) References Cited

U.S. PATENT DOCUMENTS

| | | | |
|---|---|---|---|
| 6,135,953 A | 10/2000 | Carim | |
| 6,223,088 B1 * | 4/2001 | Scharnberg | A61N 1/0492 607/152 |
| 6,308,105 B1 | 10/2001 | Duysens et al. | |
| 6,321,103 B1 * | 11/2001 | Dowd | A61B 5/288 439/669 |
| 6,343,233 B1 | 1/2002 | Werner et al. | |
| 6,415,170 B1 * | 7/2002 | Loutis | A61N 1/048 600/397 |
| 6,496,727 B1 * | 12/2002 | Bernhard | A61N 1/30 604/20 |
| 7,346,380 B2 * | 3/2008 | Axelgaard | A61N 1/0496 607/152 |
| 7,627,384 B2 | 12/2009 | Ayal et al. | |
| 7,797,058 B2 | 9/2010 | Mrva et al. | |
| 7,819,710 B2 * | 10/2010 | McIntire | A61B 5/061 439/890 |
| 8,123,576 B2 * | 2/2012 | Kim | A61B 5/274 600/394 |
| 8,197,844 B2 * | 6/2012 | Yanaki | A61N 1/30 600/386 |
| 8,251,736 B2 * | 8/2012 | McIntire | H01R 4/48 439/357 |
| 8,406,843 B2 * | 3/2013 | Tiegs | A61B 5/274 600/394 |
| 8,660,668 B2 * | 2/2014 | Bardy | A61N 1/3956 607/116 |
| 8,868,211 B2 | 10/2014 | Durand et al. | |
| 8,868,217 B2 * | 10/2014 | Dar | A61N 1/0452 600/386 |
| 9,114,250 B2 | 8/2015 | True et al. | |
| 9,226,680 B1 | 1/2016 | Kendricks | |
| 9,227,053 B2 | 1/2016 | Bonde et al. | |
| 9,283,379 B2 | 3/2016 | True et al. | |
| 9,737,225 B2 * | 8/2017 | Datta | A61B 5/274 |
| 10,376,218 B2 * | 8/2019 | Zdeblick | A61J 7/0481 |
| 10,413,183 B2 * | 9/2019 | Antonio | A61B 5/1486 |
| 10,729,342 B2 * | 8/2020 | Cantwell | A61B 5/6884 |
| 10,994,130 B2 | 5/2021 | Clements et al. | |
| 11,367,974 B1 * | 6/2022 | Judd | H01R 12/718 |
| 2001/0031988 A1 * | 10/2001 | Kurata | A61N 1/0408 607/2 |
| 2003/0088239 A1 * | 5/2003 | Takaki | A61N 1/0496 606/1 |
| 2004/0111139 A1 | 6/2004 | McCreery | |
| 2004/0176831 A1 | 9/2004 | Gliner et al. | |
| 2005/0004550 A1 * | 1/2005 | Sun | A61N 1/30 977/932 |
| 2005/0271725 A1 * | 12/2005 | Kuribayashi | A61N 1/0444 604/20 |
| 2006/0258973 A1 * | 11/2006 | Volt | A61B 17/205 604/22 |
| 2007/0032719 A1 * | 2/2007 | Menon | C09J 9/02 252/500 |
| 2007/0185432 A1 * | 8/2007 | Etheredge | A61B 17/205 604/173 |
| 2007/0282188 A1 * | 12/2007 | Copp-Howland | A61K 47/10 600/397 |
| 2008/0132773 A1 * | 6/2008 | Burnes | A61B 5/282 600/394 |
| 2009/0062721 A1 * | 3/2009 | Hayakawa | A61N 1/0436 604/20 |
| 2009/0156925 A1 * | 6/2009 | Jin | A61B 5/291 600/372 |
| 2009/0318793 A1 * | 12/2009 | Datta | A61B 5/06 600/391 |
| 2010/0082088 A1 * | 4/2010 | Fassih | A61N 1/325 607/149 |
| 2010/0145221 A1 | 6/2010 | Brunnett | |
| 2010/0145222 A1 | 6/2010 | Brunnett et al. | |
| 2010/0168831 A1 | 7/2010 | Korivi et al. | |
| 2011/0152743 A1 * | 6/2011 | Adachi | A61N 1/0448 604/20 |
| 2011/0237921 A1 | 9/2011 | Askin, III et al. | |
| 2012/0330217 A1 * | 12/2012 | Hasui | A61N 1/0448 604/20 |
| 2013/0066183 A1 * | 3/2013 | Jin | A61B 5/291 600/383 |
| 2013/0304175 A1 * | 11/2013 | Voegele | A61N 1/0408 607/152 |
| 2013/0338749 A1 | 12/2013 | Brunnett et al. | |
| 2014/0135887 A1 * | 5/2014 | Totman | A61N 1/0492 607/142 |
| 2014/0142410 A1 | 5/2014 | Erb et al. | |
| 2015/0173681 A1 * | 6/2015 | Hammerling | A61B 5/031 600/386 |
| 2016/0058380 A1 | 3/2016 | Lee et al. | |
| 2016/0120475 A1 | 5/2016 | Cha et al. | |
| 2017/0197076 A1 | 7/2017 | Faltys et al. | |
| 2017/0216584 A1 * | 8/2017 | Chun | A61N 1/303 |
| 2017/0266436 A1 | 9/2017 | Suwito et al. | |
| 2017/0281926 A1 * | 10/2017 | Martins | C09J 7/21 |
| 2017/0332967 A1 * | 11/2017 | Hatori | A61B 5/296 |
| 2017/0340232 A1 | 11/2017 | Stewart | |
| 2017/0368329 A1 * | 12/2017 | Tyler | G10L 15/02 |
| 2018/0085573 A1 * | 3/2018 | Alam | A61N 1/36071 |
| 2019/0022400 A1 * | 1/2019 | Kumar | A61B 5/361 |
| 2019/0104995 A1 * | 4/2019 | Cantwell | A61B 5/6882 |
| 2021/0228441 A1 * | 7/2021 | Giacometti | A61B 5/1121 |
| 2021/0244332 A1 * | 8/2021 | Hagihara | D03D 15/00 |

FOREIGN PATENT DOCUMENTS

| | | | |
|---|---|---|---|
| FR | 2372636 A1 | 6/1978 | |
| GB | 2131297 A * | 6/1984 | A61B 5/0416 |
| GB | 2351911 A | 1/2001 | |
| KR | 2012-0096675 A | 8/2012 | |
| WO | 94/22365 | 10/1994 | |
| WO | 2009135138 A1 | 11/2009 | |
| WO | 2014055393 A1 | 4/2014 | |
| WO | 2018045056 A1 | 3/2018 | |

OTHER PUBLICATIONS

PCT Search Report dated Apr. 5, 2019 for PCT/US2018/065326 (18 pages).

Hoffer et al., Ch. 5, "How to Use Nerve Cuffs to Stimulate, Record or Modulate Neural Activity," Neural Prostheses for Restoration of Sensory and Motor Function, CRC Press, pp. 139-175 (2001).

San Martin, "Protocol for Neurophysiological Studies of the Superior and Recurrent Laryngeal Nerves and of the Cricothyroid and Thryoarytenoid Muscles," J. Otolaryngology—ENT Research, vol. 6, Issue 1, pp. 1-10 (Jan. 30, 2017).

Chiang et al., "Comparison of EMG signals recorded by surface electrodes on endotracheal tube and thyroid cartilage during monitored thyroidectomy", KJMS (May 15, 2017) 33, 503-509.

APS Electrode YouTube video, https://www.youtube.com/watch?v=LUomWViTnVA, published on Dec. 10, 2014.

C.F. Sinclair et al., "Contralateral R1 and R2 Components of the Laryngeal Adductor Reflex in Humans Under General Anesthesia", The Laryngoscope, 127 12, E443-E448 (2017).

PCT Search Report dated Dec. 20, 2018 for PCT/US2018/054530 (13 pages).

C. Dionigi et al., "Continuous Intraoperative Neuromonitoring (C-IONM) Technique with the Automatic Periodic Stimulating (APS) Acessory for Conventional and Endoscopic Thyroid Surgery", General Surgery, Surgical Technology International XXVI, May 26, 2015, pp. 101-114.

Japan Patent Office Notice of Reasons for Rejection (Office Action) issued against JP Patent Application No. 2020-516544, dated Oct. 7, 2022.

China—Notice of the First Office Action, China Application No. 201880058050.1, Date of Dispatch Nov. 3, 2022.

(56) References Cited

OTHER PUBLICATIONS

Chinese Notice of the Second Office Action corresponding to Chinese Patent Application No. 201880058050.1, dated Apr. 13, 2023, with Search Report.

* cited by examiner

PLEDGET STIMULATION AND RECORDING ELECTRODE ASSEMBLIES

CROSS-REFERENCE TO RELATED APPLICATIONS

This non-provisional application claims the benefit of U.S. Application Ser. No. 62/568,841, filed Oct. 6, 2017.

FIELD

The present technology is generally related to stimulation and recording electrode assemblies as well as methods of conducting an intraoperative tissue monitoring and/or stimulation procedure.

BACKGROUND

Nerve monitoring is used in surgical procedures where nerves are at risk. With some systems, a nerve integrity monitor and a hand held stimulator probe provide intermittent stimulation only when the surgeon probes the nerve. Nerves can be at risk, however, in between stimulations due to surgical incision "blind" trauma caused by manipulation and stretching during tumor removal, and cumulative trauma or damage that may result in neurapraxia. Automatic periodic stimulation (APS), however, provides Continuous Intraoperative Nerve Monitoring (CIONM). Intraoperative NIM nerve monitoring systems enable surgeons to identify, confirm, and monitor motor nerve function to help reduce the risk of nerve damage during various procedures including ENT and general surgeries.

One such system is Medtronic, Inc.'s NIM® Nerve Monitoring System, which includes an electromyographic (EMG) monitor for intraoperative use during various surgeries in which a nerve may be at risk due to unintentional manipulation. NIM nerve monitoring probes having electrodes are placed in the appropriate muscle locations in the patient for the procedure being performed. These electrodes are connected to the NIM Nerve Monitoring System, which continuously monitors EMG activity from muscles innervated by the affected nerve. When a particular nerve has been activated or stimulated, the NIM® System warns the surgeon and operating room staff, providing both visual alerts on the color touchscreen monitor and audio feedback to help minimize trauma to the nerve.

Surgeons can use monopolar and bipolar stimulating probes and dissection instruments with the NIM® Nerve Monitoring System to assist in early nerve identification and confirmation. These tools may be used to locate, identify, and map the particular nerve and branches, as well as verify nerve function and integrity to help surgeons perform critical procedures while preserving nerve function and improving patient safety.

The present disclosure provides improvements associated with the related art.

SUMMARY

Aspects of this disclosure generally relate to stimulation and/or recording electrode assemblies that can be affixed to bioelectric tissue, such as a nerve, without the use of adhesive.

Aspects of the disclosure are related to stimulation and/or recording electrode assemblies and systems that are particularly useful for Automatic Periodic Stimulation (APS). Such embodiments are compatible with nerve monitoring systems to provide continuous stimulation of a nerve during surgery. Disclosed embodiments are useful for evoked potential monitoring throughout the body including cranial and peripheral and mixed motor-sensory nerves during surgery, including spinal cord and spinal nerve roots. Disclosed embodiments are useful for stimulation, biopotential recording, therapeutic stimulation and automatic periodic stimulation (APS) to nerves during evoked potential monitoring procedures including but not limited to: intracranial, extracranial, intratemporal, extratemporal, neck dissections, thoracic surgeries, and upper and lower extremities, degenerative treatments, pedicle screw procedures, fusion cages, rhizotomy, orthopedic surgery, open and percutaneous lumbar and cervical surgical procedures, and thoracic surgical procedures.

Aspects of the disclosure include an intraoperative electrode assembly having a pledget substrate made at least partially of a material that is hydrophilic as well as one or more electrodes supported by and positioned within the pledget substrate. In various embodiments, the material is a rayon/polyethylene terephthalate blend. The electrode assembly further includes a lead wire assembly interconnected to each electrode. In various embodiments, the lead wire assembly includes at an insulating jacket positioned around a wire core and the electrode assembly further including an insulating cup interconnecting the electrode and the insulating jacket. The cup may be configured to rotate about the pledget substrate. In some embodiments, the pledget substrate includes two separable bodies, each including an electrode.

Aspects of the disclosure also include methods of conducting an intraoperative procedure. The methods include providing an electrode assembly including, a pledget substrate having a first surface that is hydrophilic, one or more electrodes supported by and positioned within the pledget substrate, and a lead wire assembly interconnected to the electrode(s). The method continues by creating an incision to access tissue of a patient and applying the pledget substrate to the tissue. Then, the one or more electrodes can be activated. Activating the electrode(s) can include recording bioelectric responses of the tissue sensed from the electrode(s). In alternate embodiments, activating the electrode(s) can include stimulation of bioelectric tissue applied from the electrode(s).

The disclosed embodiments provide for continuous intraoperative monitoring in current and new procedures that place nerves at risk without extra dissection or wrapping of the electrode assembly around the entirety of the respective nerve. In this way, the disclosed embodiments are more easily applied to a nerve, thus requiring less skill (either actual or perceived) from the clinician.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1A:
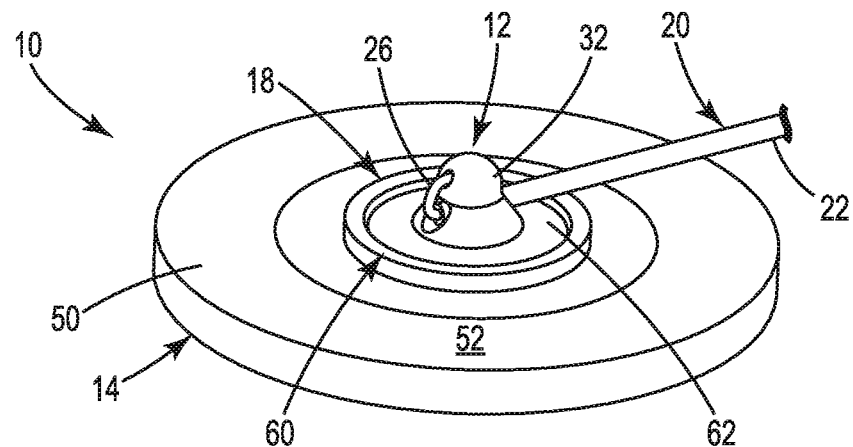
FIG. 1A is a perspective top view of one embodiment of an electrode assembly.

Nerve monitoring is used in surgical procedures where nerves are at risk. A system including a nerve integrity monitor and a hand held stimulator probe having an electrode provides intermittent stimulation only when the surgeon probes the nerve. Nerves can be at risk, however, in between stimulations due to surgical incision "blind" trauma caused by manipulation and stretching during tumor removal, and cumulative trauma or damage that may result in neuropraxia. Automatic periodic stimulation (APS), however, provides continuous intraoperative nerve monitoring (CIONM). The electrode provides continuous, periodic stimulation of nerve used for trending amplitude and latency in real time which includes adjustable alarm limits for significant baseline changes. This early warning helps alert the surgeon to stop surgical trauma as most injury is immediacy reversible but can become permanent if prolonged.

Aspects of the disclosure relate to pledget stimulation and recording electrode assemblies that are particularly useful with APS, for example. Such embodiments are compatible with nerve monitoring systems to provide continuous nerve stimulation during a surgical procedure. Two compatible nerve monitoring system include NIM Eclipse® (Part number 945NCCPUE4), NIM-Response® 3.0 (Part number 8253001) and NIM-Neuro® 3.0 nerve (part number 8253401) monitoring systems all available from Medtronic, Inc. of Minneapolis, Minn. The disclosed electrode assemblies are particularly useful for monitoring a facial nerve at a main trunk in head and neck procedures, as well as the facial nerve in lateral skull base procedure (LSB) procedures. The electrode assembly can be used for short procedures less than 24 hours or implanted in the patient longer than 24 hours. An electrode surface of the electrode assembly may be coated to deliver a drug during contact or enhanced treatment such as through electro-paresis. Other disclosed embodiments are particularly useful for thyroid laryngeal monitoring without an electromyogram (EMG) endotracheal tube. Such an electrosurgical endotracheal tube is disclosed in McFarlin et al., U.S. patent application Ser. No. 16/108,682, filed Aug. 22, 2018, the entire contents of which are herein incorporated by reference in its entirety. The electrode assemblies of the disclosure can be used in evoked potential intraoperative monitoring systems during surgical procedures and are an alternative which simplifies stimulation of tissue over current methods including cuffed APS electrodes or needle electrodes used for stimulation. The electrode assemblies of the present disclosure simplify recording of tissue over such current methods. Examples of such current methods are more thoroughly disclosed in Sinclair, C. F., Téllez, M. J., Tapia, O. R., & Ulkatan, S. (2017). Contralateral R1 and R2 components of the laryngeal adductor reflex in humans under general anesthesia. *The Laryngoscope,* 127 12, E443-E448. The use of the disclosed embodiments, however, is not intended to be limited to any specific procedure and examples of particular systems in which the electrode assemblies can be incorporated and methods of use will be further disclosed below.

Figure 1B:
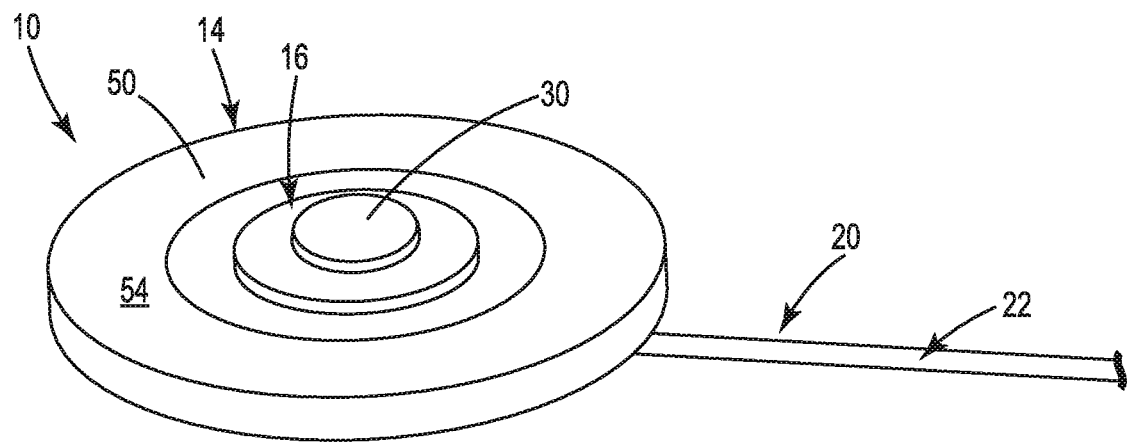
FIG. 1B is a perspective bottom view of the electrode assembly of FIG. 1A.
Figure 1C:
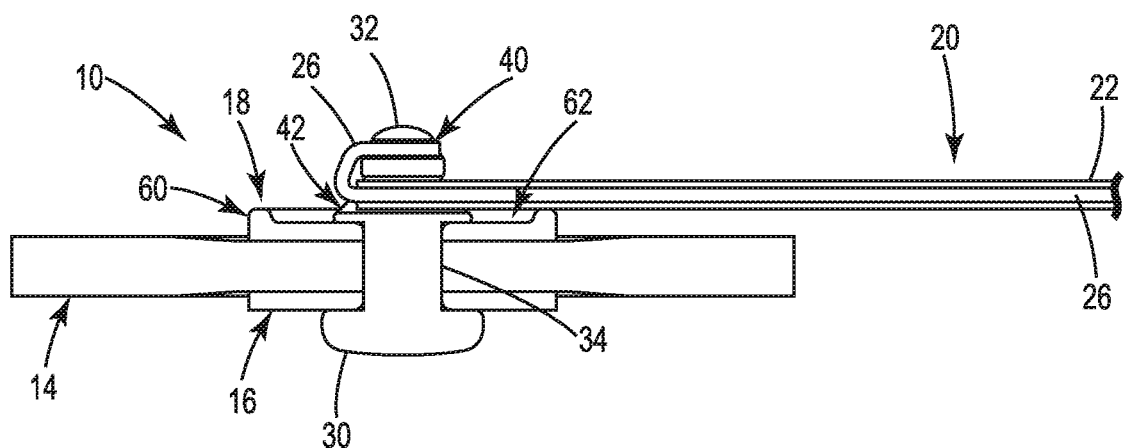
FIG. 1C is a cross-sectional view of the electrode assembly of FIGS. 1A-1B.

One example embodiment of an electrode assembly 10 is illustrated in FIGS. 1A-1C. The electrode assembly 10 includes one or more electrodes 12 supported by and positioned within a pledget substrate 14 with one or more spacers 16, 18. In one embodiment, the one or more electrodes 12 are evoked potential monitoring electrodes. The electrode assembly 10 further includes a lead wire assembly 20 including at least one insulating jacket 22 positioned around a wire core 26.

The electrode 12 can be used as recording and stimulating electrode as well as therapeutic stimulating electrode. In some embodiments, as further disclosed below with respect to FIG. 6, for example, two electrodes can be provided to provide bipolar stimulation or recording and is configured to communicate electrical stimulus to tissues and thus must provide the appropriate surface area for contacting tissue for the current density. The material in which the electrode 12 is formed or surface treatment (not shown) provided on the electrode 12 at the base 30 (or interface at which the electrode 12 contacts the nerve or other bioelectric tissue) can be selected to enhance the bioelectric interface to tissue via selection of such preferred base metals, sintering to increase surface area, or plaiting. Suitable material examples for the electrode 12 at the interface or base 30 include stainless steel, copper, gold, iridium, palladium, platinum, rubidium, ruthenium, silver, conductive plastics or inks. Conductive plastics or inks can be used on the surface of the top 32 or base 30 to enhance conductions delivery to the tissue. For example, a conductive ink may have about 40-60% conductive silver particles with polyvinylchloride (PVC) particles with a solvent that evaporates to dry the ink on a surface of the electrode 12. Conductive plastic constructed of conductive particles and polymeric particles are fused together to form a conductive plastic.

Figure 2A:
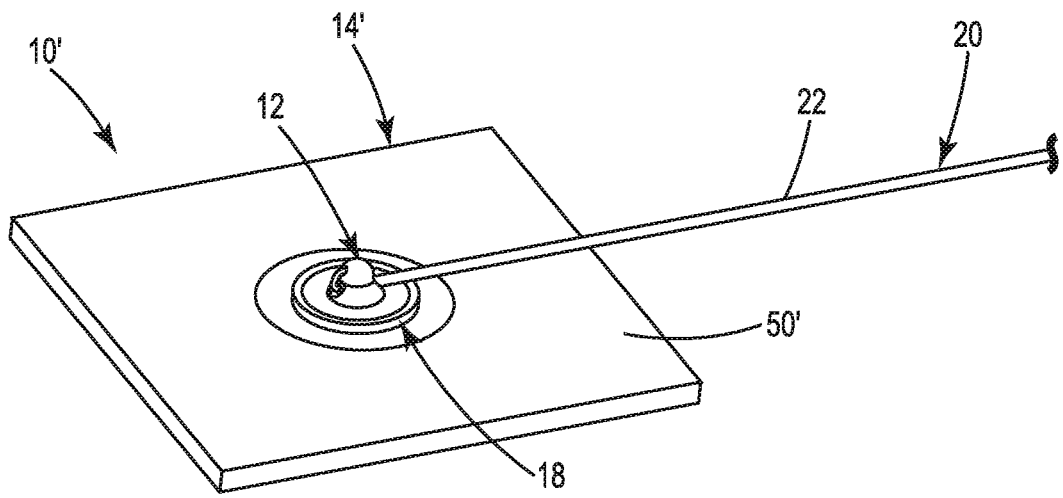
FIG. 2A is a perspective top view of another embodiment of an electrode assembly.
Figure 2B:
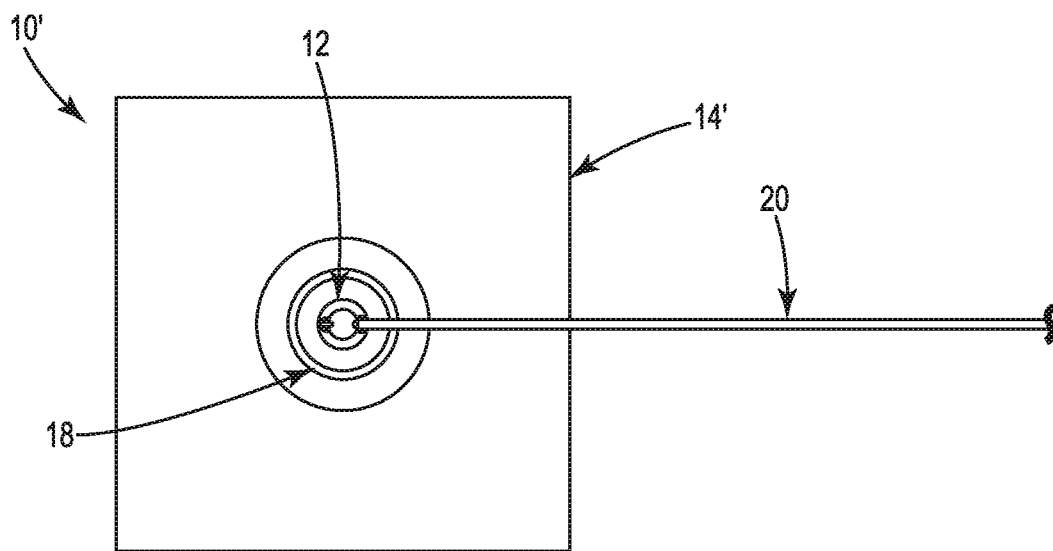
FIG. 2B is a perspective bottom view of the electrode assembly of FIG. 2A.
Figure 2C:
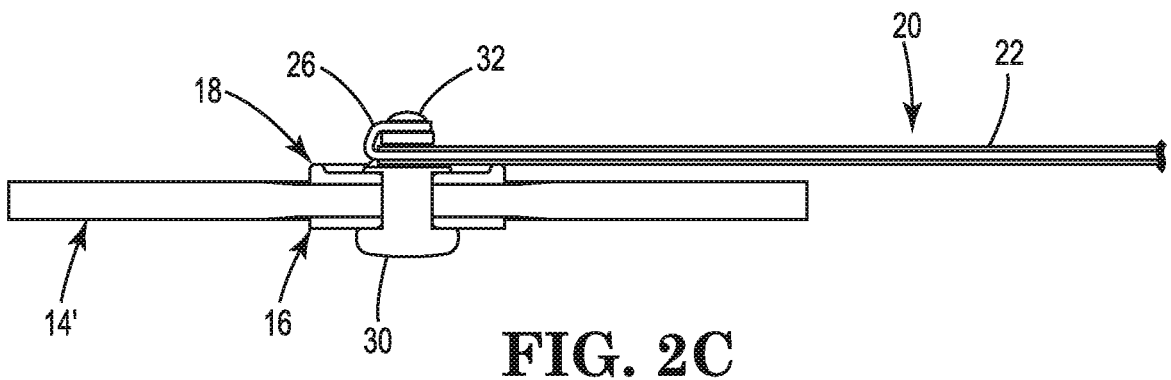
FIG. 2C is a cross-sectional view of the electrode assembly of FIGS. 2A-2B.

The electrode 12 is also configured to allow for crimping and strain relief of the lead wire assembly 20. As also shown in FIGS. 2A-2B, the electrode 12 can be configured to include a base 30, a top 32, and an axle 34 interconnecting the top 32 and the base 30. Such features capture the spacers 16, 18 and pledget substrate 14. Moreover, the top 32 can include a domed portion 36 interconnected to a flanged portion 38 extending outwardly with respect to the domed portion 36 and the axle 34. The top 32 includes first and second channels 40, 42, which are configured to retain portions of the lead wire assembly 20. In one embodiment, the first channel 40 is positioned within the domed portion 36 and can be crimped to the exposed wire core 26 proximate the top 32 using a single point crimp. The second channel 42 can be used to provide strain relief within the wire core 26 and can optionally be positioned to extend within the flanged portion 38. In certain embodiments, the top 32 is configured to provide a low profile wire core 26 interface. In the illustrated embodiment, the first channel 40 is configured to retain both the jacket 22 and the wire core 26 and the second channel 42 is configured to retain only the wire core 26. The electrode 12 can be made of an adhesive compatible material or can otherwise provide an adhesive compatible surface so that the wire core 26 can be secured to the top 32 of the electrode 12 with adhesive (not shown).

The base 30 can optionally contain or have applied thereto a bioactive agent or therapeutic (drug or anesthetic) which delivery can be enhanced by iontophoresis. Examples of bioactive agents include, but are not limited to, steroids dexamethasone, and methylprednisolone or anesthetic agents such as lidocaine xylocaine epinephrine. The electrode 12 can aid in applying such local drug or anesthetics to selected locations which the electrode 12 (coupled with a current return electrode) delivers the externally applied potential difference where the movements of ions across a membrane enhanced using for therapeutic purposes.

Although not shown, the electrode 12 can optionally be selectively electrically insulated. In such embodiments, the electrode 12 can be coated in an insulator completely (e.g., using chemical vapor deposition). This coating can then be selectively removed (e.g., using a laser) to expose desired areas. Alternatively, the electrode 12 can be masked and then an insulating coating can be applied.

The pledget substrate 14 includes a round shaped body 50 of material that affixes from surface tension via Van der Waals forces or bio adhesion such as tissue clotting, drying or scar tissue healing, for example, and is configured to maintain fixation to a nerve/tissue under wet conditions. In various embodiments, the pledget substrate 14 is configured to interface with nerves within the range of about 1 mm to about 4 mm. Further, the pledget substrate 14 is free to rotate with respect to both of the wire core 26 of the lead wire assembly 20 and the electrode 12. The body 50 is made of a porous material to allow for suction of fluids and may be provided with a coating (not visible) including of an aqueous solution of binder, water and a surfactant, which ties down the surface fibers of the body 50 and eliminates fraying of the body 50 while providing additional strength to the body 50 for its application to bioelectric tissue. The coating can further include a pigment to provide chromatic differentiation of a stimulation or nerve side of the pledget substrate 14. In this way, a first side 52 of the body 50 can include a coating of a first color and a second side 54 of the body 50 can include a coating of a second color or, alternatively, no color. In some embodiments, the tissue/stimulating side 54 coating may be hydrophilic while the, opposing, side 52 of the pledget substrate 14 may have a hydrophobic coating to enhance electrical current steering. It is desirable that the body 50 be made of a lint-free material that maintains a high degree of absorbency. One example of a suitable material for the body 50 is spunbond rayon (about 0.33 mm thick). Other suitable materials include rayon/polyethylene terephthalate (PET) blends and PET/viscose blends, for example. Tests evaluating suitable materials for the pledget substrate 14, and any alternate pledget substrates disclosed herein, are further discussed below with respect to Tables 5-14.

Figure 1D:
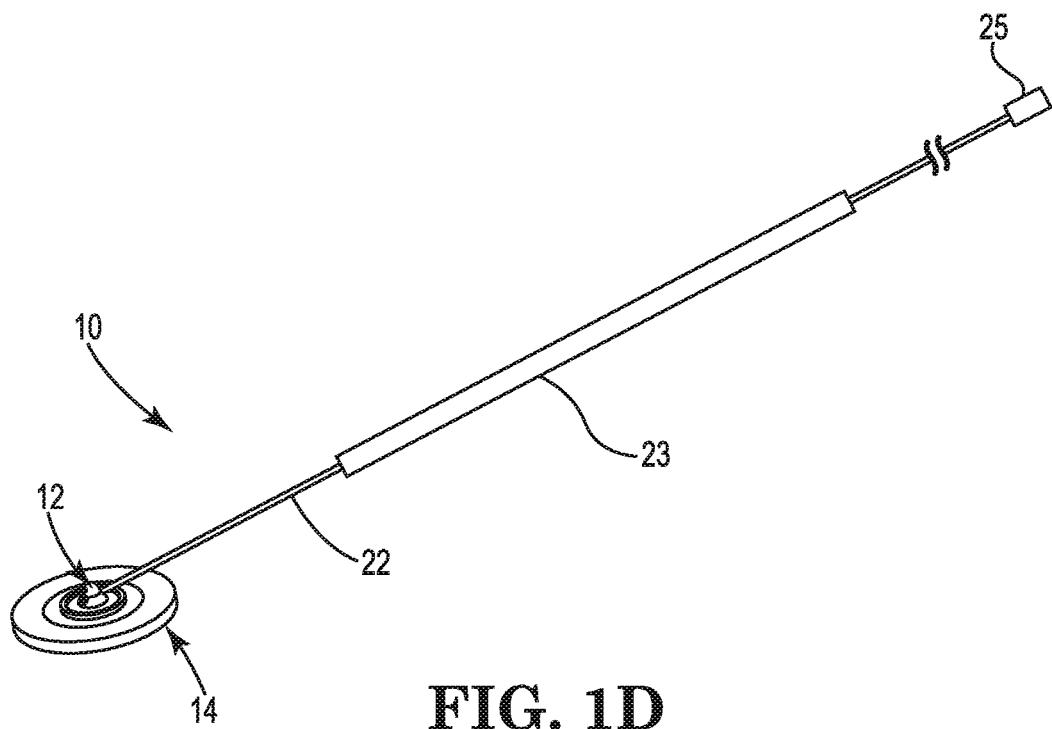
FIG. 1D is an additional perspective view of the electrode assembly of FIGS. 1A-1C.

The lead wire assembly 20 can optionally further include a sleeve 23 as is visible in FIG. 1D. The sleeve 23 can be made of a material such as cotton or the like, which allows the clinician to stick the lead wire assembly 20 to a portion of a patient's anatomy (not shown). In such embodiments, the sleeve 23 can be optionally slidable along a length a of the jacket 22 so that the sleeve 23 can be selectively positioned at a portion along the jacket 22, wetted with water or the like, and then pressed onto the anatomy to facilitate adhesion of the sleeve 23 (and thus adhesion of the lead wire assembly) to the anatomy. The lead wire assembly 20 additionally includes a connector 25 configured to be connected to a nerve monitoring system such as those disclosed herein, for example, configured to activate the electrode(s) 12 to record bioelectric responses of the tissue sensed from the electrode 12 (see also, FIGS. 17-21). In alternate embodiments, stimulation of bioelectric tissue from the electrode(s) 12.

As generally illustrated in FIGS. 2A-2B, an electrode assembly 10' of the present disclosure need not include a pledget substrate 14' including a body 50' having a round shape and can have an alternate shape, such as a square shape. Other shapes, including irregular shapes, are envisioned. As indicated with like reference numerals referring to like features as described herein, all other aspects of the electrode assembly 10' can be configured similarly and operate in ways described above with respect to the embodiment 10 of FIGS. 1A-1C except as explicitly stated.

As shown, the electrode assembly 10 of the disclosed embodiments can have two spacers 16, 18 including the first spacer 16 and the second spacer 18 located on opposing sides of the pledget substrate 14. The first spacer 16 includes an aperture (not clearly visible) through which the electrode 12 is positioned. The first spacer 16 can provide strain relief within the pledget substrate 14 and also provides electrical current directivity and insulation between the electrode axle 34 and pledget substrate 14. In one example embodiment, the first spacer 16 is made of polyethylene. The second spacer 18 also defines an aperture (not clearly visible) through which the electrode axle 34 is positioned. The second spacer 18 can also provide strain relief within the pledget substrate 14 and provide for free rotation of the pledget substrate 14 about the electrode 12 as well as surface for adhesion of the body 50. The second spacer 18 additionally provides electrical current directivity, chromatic differentiation of stimulating and nerve sides of the pledget substrate 14, allows the electrode 12 and wire core 26 to rotate freely and can include a feature 60, which enhances the ability to manipulate the electrode 12. In one example, the feature 60 is a lip that can be grabbed by a standard surgical instrument. The second spacer 18 further includes a retaining structure 62, such as a bowl, that can at least in part be defined by the feature 60, to retain liquid adhesive (not shown) used to secure the top 32 of the electrode 12 to the wire core 26 after the adhesive dries or is cured. In one example embodiment, the second spacer 18 can be made of nylon.

Figure 3B:
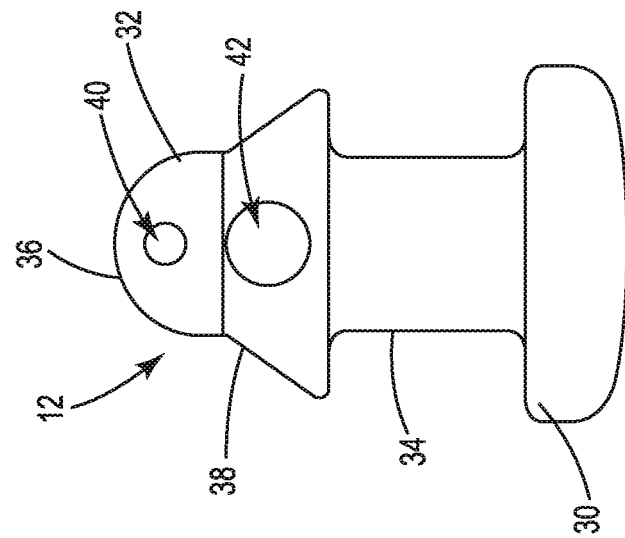
FIG. 3B is an alternate perspective view of the electrode of FIG. 3A.
Figure 3A:
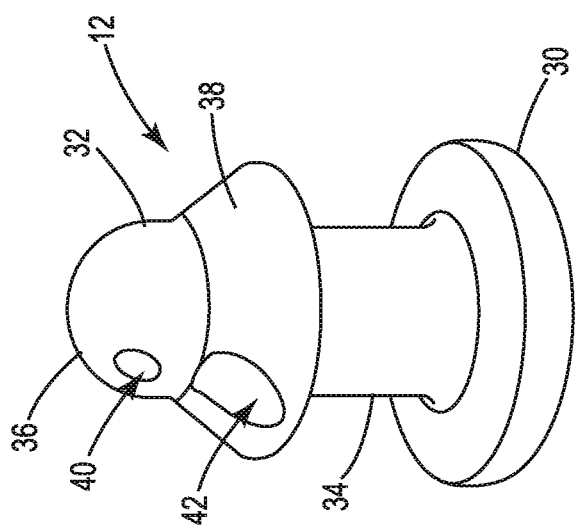
FIG. 3A is a perspective view of an electrode that can be used in the embodiments of FIGS. 1A-2C.
Figure 4A:
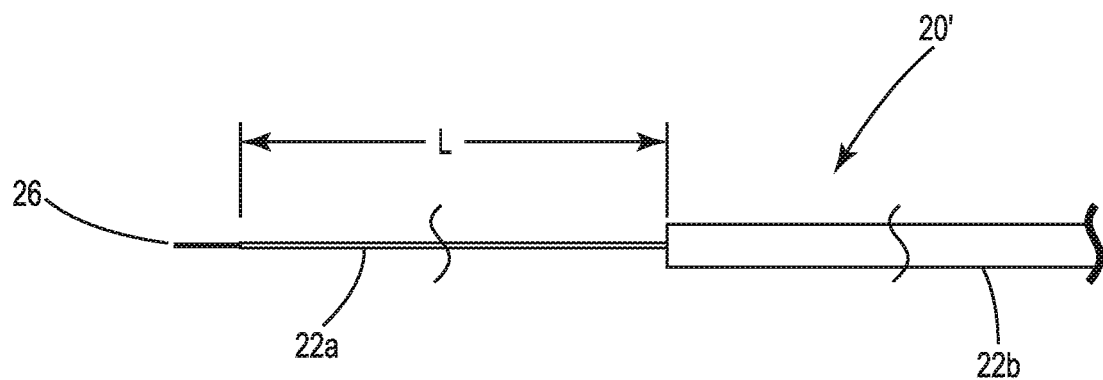
FIG. 4A is a side view of a lead wire assembly that can be used in the embodiments of FIGS. 1A-2C.
Figure 4B:
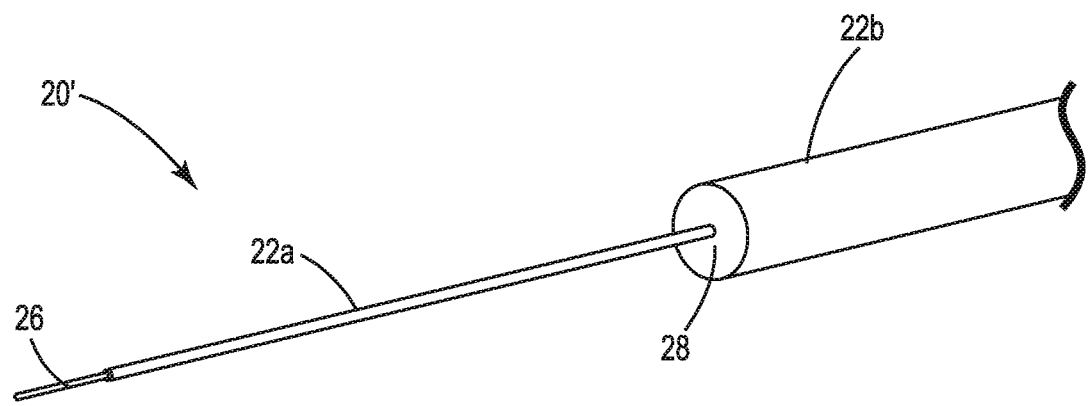
FIG. 4B is a perspective view of the lead wire assembly of FIG. 4A.

Turning now also to FIGS. 3A-3B, which illustrate an alternate lead wire assembly 20'. The lead wire assembly 20' is substantially similar to the lead wire assembly 20 discussed herein but instead of only including a single insulating jacket (e.g., jacket 22), the lead wire assembly 20' includes an inner jacket 22a, outer jacket 22b surrounding the wire core 26. Both of the inner and outer jackets 22a, 22b can optionally be provided to insulate the wire core 26 and to eliminate a potential need to splice the lead wire assembly 20. In this way, the outer jacket 22b can be at least partially stripped from the inner jacket 22a. In addition, a release agent 28 such as silicone or the like can be applied between the inner and outer jackets 22a, 22b to prevent adhesion between the inner and outer jackets 22a, 22b. In some embodiments, a length L of approximately 6 inches of the inner jacket 22a will be exposed with respect to the outer jacket 22b.

The lead wire assemblies 20, 20' are malleable and pliable having a thread-like flexibility while having a high-tensile strength. In some embodiments, the lead wire assembly 20, 20' can support at least 0.5 lb. break strength. Where provided, the inner and outer jackets 22a, 22b (or single jacket 22) provides electrical insulation to the wire core 26 and, in some embodiments, is or are collectively thin to maintain flexibility of the lead wire assembly 20 or jacket 22, 22a/22b. In one example embodiment, the jacket 22 or outer jacket 22b is made of a low-reflectivity material such as polyvinyl chloride (PVC) and provides electrical insulation of 1000 VC dielectric strength. Where provided, the inner jacket can be made of polytetrafluoroethylene (PTFE), for example. The wire core 26 is malleable to retain a deformed shape and can optionally be made of 300 series stainless steel 40AWG single strand material. The jacket(s) 22, 22a, 22b can be of a specific color, such as yellow to provide contrast with a patient's anatomy. As shown with respect to the lead wire assembly 20 in FIG. 5, the lead wire assembly 20, 20' can further support electrical connections to the electrode 12 and/or APS system, for example, via a pin jack 70 or the like that provides the electrical communication a patient interface (not shown). The pin jack 70 can be protected for International Electrotechnical Commission 60601 compliance.

Figure 5:
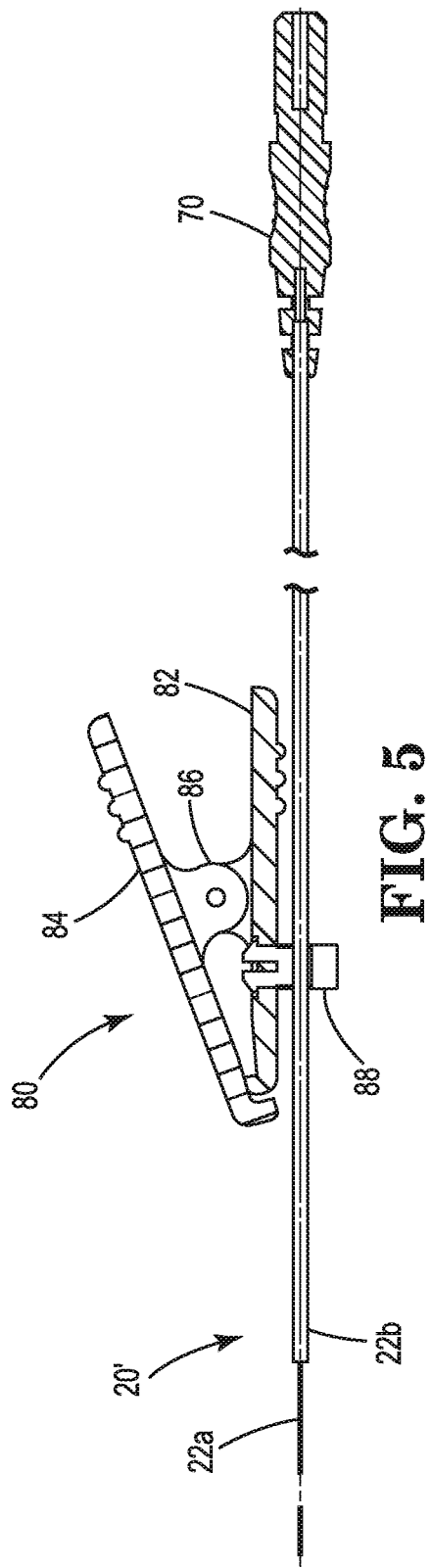
FIG. 5 is a cross-sectional view of a clip and a pin interconnected to the lead wire assembly such as that of FIGS. 4A-4B.

As generally illustrated in FIG. 5, a clip 80 can be secured to the lead wire assembly 20' (or the lead wire assembly 20 in a similar fashion) to secure the lead wire assembly 20' to an ear of the patient or, a sterile drape that covers the patient during surgery, for example, to provide strain relief. The clip 80 can be configured to include two arms 82, 84 that include a hinged connection 86 biased in the closed position. The hinged connection 86 can include a pin about which the two arms 82, 84 can rotate. The two arms 82, 84 can be spring biased into the closed position. The clip 80 includes a mounting block 88 that secures one arm 82 to the jacket 22b. The mounting block 88 can be configured to allow the clip 80 to slide along a length of the lead wire assembly 20' with light resistance (e.g., 0.3 lbs. or less). In addition, the mounting block 88 can be connected to the clip 80 as to allow the clip 80 to rotate or spin 360 degrees with respect to the mounting block 88.

Figure 6:
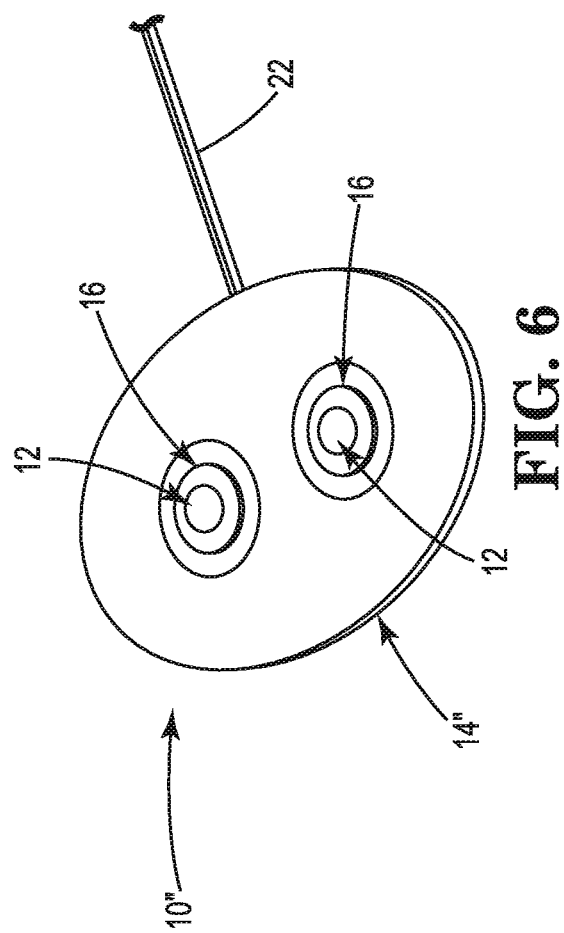
FIG. 6 is a perspective view of an alternate electrode assembly, which is largely similar to embodiments previously illustrated but wherein the electrode assembly includes two electrodes.

As previously suggested with respect to the embodiment of FIGS. 1A-1D, in an alternate electrode assembly, the electrode assembly can include a plurality of electrodes 12. FIG. 6 illustrates an electrode assembly 10" including two spaced apart electrodes 12 supported in a generally oval-shaped pledget substrate 14". Each electrode 12 is connected and supported within the pledget substrate 14" with one or more spacers 16 and further in ways described above with respect to other embodiments. As indicated with like reference numerals referring to like features as described herein, all other aspects of the electrode assembly 10", including other properties of the pledget substrate 14", can be configured similarly and operate in ways described above with respect to the embodiments 10 or 10' of FIGS. 1A-5 except as explicitly stated to differ.

Turning now also to FIGS. 7A-10, which illustrate an alternate electrode assembly 110. The electrode assembly 110 includes an evoked potential monitoring electrode 112 supported by and positioned within a pledget substrate 114 with a hub 160 having an aperture 162 and first and second flanges 164a, 164b extending radially from the aperture 162. The hub 160 is over-molded to the pledget substrate 114 and is made of a rigid material, such as polyethylene, and optionally includes a color pigment, for example. The hub 160 is believed to improve the physical retention of the pledget substrate 114 by retaining and encapsulating fibers of the pledget substrate 114 material. The hub 160 further is configured to provide for free rotation of the pledget substrate 114 about the hub 160/electrode 112 and reduces deformation of the pledget substrate 114 due to lateral stresses imparted on the pledget substrate 114.

As with prior embodiments, the electrode 112 can be used as recording and stimulating electrode as well as therapeutic stimulating electrode. In some embodiments, as previously discussed with respect to FIG. 6, two electrodes can be provided in the electrode assembly 110. Each electrode 112 can include a base 130 configured for contact with tissue and an axle 134 extending therefrom. A channel 142 extends within the axle 134 and is configured to receive the wire core 126 of the lead wire assembly 120. As can be seen in FIG. 7C, the axle 134 and the first portion 192 of cup 190 are configured such that the axle 134 can be positioned within the channel 196. The material in which the electrode 112 is formed or surface treatment (not shown) provided on the base 130 of the electrode 112 (or interface at which the electrode 112 contacts the tissue) can be selected to enhance the bioelectric interface to tissue via selection of such preferred base metals, sintering to increase surface area, or plaiting. In the illustrated embodiment, the axle 134 and optionally a portion of the base 130 includes a selectively-applied coating 139 applied exterior to a channel 142 extending through the axle 134. The coating 139 eliminates shunting and ensures that all of the stimulation current is delivered to the base 130 of the electrode 112 and, therefore, delivered to the contacting tissue. This improves the consistence of the electrode assembly 110 performance in both bloodless "dry" and flooded "wet" surgical fields. In addition, this configuration provides a smooth, low-friction surface about which the hub 160 can rotate within the pledget substrate 114. Moreover, the selectively-applied coating 139 ensures electrical conductivity in the crimped and nerve contacting areas while electrically insulating all other surfaces of the electrode 112. Examples of suitable materials for the coating 139 include, but are not limited to, fluoropolymer, diamond-like-coating (DLC), parylene silicone dioxide, aluminum oxide, halar, cured photopolymer, ceramic and polyimide coatings. Suitable material examples and other properties for the electrode 112 can be similar to those disclosed with respect to electrode 12 except as expressly stated.

The electrode assembly 110 further includes a lead wire assembly 120 including at least one insulating jacket 122 positioned around a wire core 126. In one example embodiment, the at least one insulating jacket 122 includes an inner polyester layer and an outer woven nylon layer positioned over the wire core 126 as is illustrated in FIG. 7C. To minimize the volume of adhesive (not shown) required to pot the electrode 112 and wire core 126, the electrode assembly 110 is provided with a cup 190. The cup 190 can be made of nylon, optionally including pigment, and includes a first portion 192 and a second portion 194. A channel 196 sized to receive the lead wire assembly 120 extends through both the first and second portions 192, 194. The first portion 192 defines a generally circular perimeter and includes a plurality of recesses or landing zones 198a-c, which provide grips for interfacing with standard surgical instruments for manipulation both during assembly and use. In one embodiment, the landing zones 198a-c are spaced approximately 120 degrees from one another. The second portion 194 can optionally include a textured surface 200.

The pledget substrate 114 includes a round or other shaped body 150 of material that affixes to patient tissue from surface tension via Van der Waals forces or bio adhesion such as tissue clotting, drying or scar tissue healing, for example, and is configured to maintain fixation to a nerve/tissue under "wet" conditions. In various embodiments, the pledget substrate 114 is configured to interface with nerves within the range of about 1 to about 4 mm. Further, the pledget substrate 114 is free to rotate with respect to both of the wire core 126 of the lead wire assembly 120 and the electrode 112. The body 150 is made of a porous material to allow for suction of fluids and may be provided with a coating (not visible) including of an aqueous solution of binder, water and a surfactant, which ties down the surface fibers of the body 150 and eliminates fraying of the body 150 while providing additional strength to the body 150 for its application to tissue. The coating can further include a pigment to provide chromatic differentiation of a stimulation or nerve side of the pledget substrate 114. In this way, a first side 152 of the body 150 can include a coating of a first color and a second side 154 of the body 150 can include a coating of a second color or, alternatively, no color. In some embodiments, the tissue/stimulating side 154 coating may be hydrophilic while the, opposing, side 152 of the pledget substrate 114 may have a hydrophobic coating to enhance electrical current steering. It is desirable that the body 150 be made of a lint-free material that maintains a high degree of absorbency. Suitable materials for the body 150 include those disclosed with respect to other embodiments herein. Except as explicitly stated, the lead wire assembly 120 can be identically configured to lead wire assemblies 20, 20' disclosed above.

Figure 11:
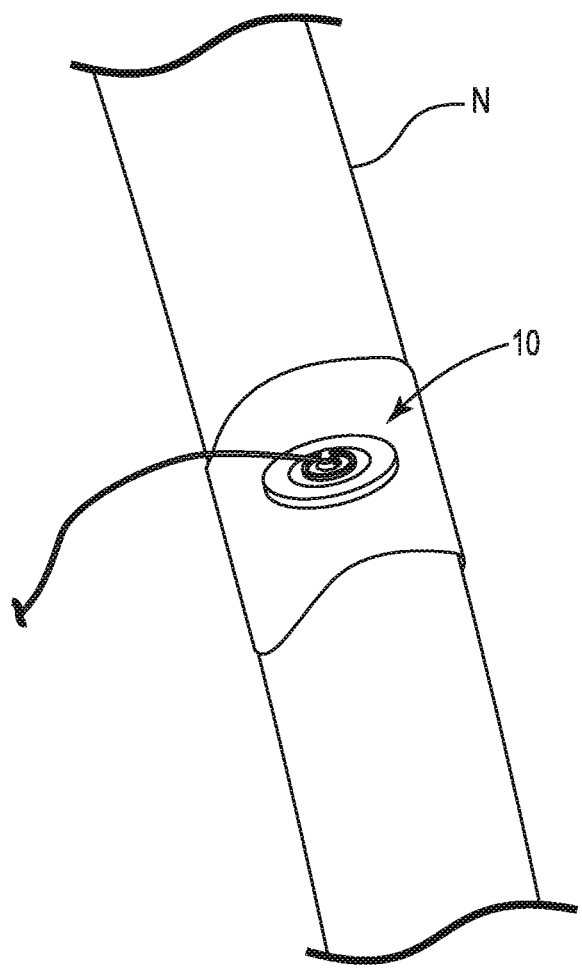
FIG. 11 is a schematic illustration of the electrode assembly of FIG. 1 wrapped around a 0.3 mm diameter nerve.

Turning now also to FIG. 11, which illustrates the electrode assembly 10 operatively affixed to a nerve N. In this illustrative example, the nerve has a 0.3 mm diameter. It will be understood that other electrode assemblies of the present disclosure can be configured to affix to the nerve N in an identical manner and that the tissue (e.g., nerve) to which the electrode assembly is applied is not to be limited to the illustrated nerve N.

Figure 12:
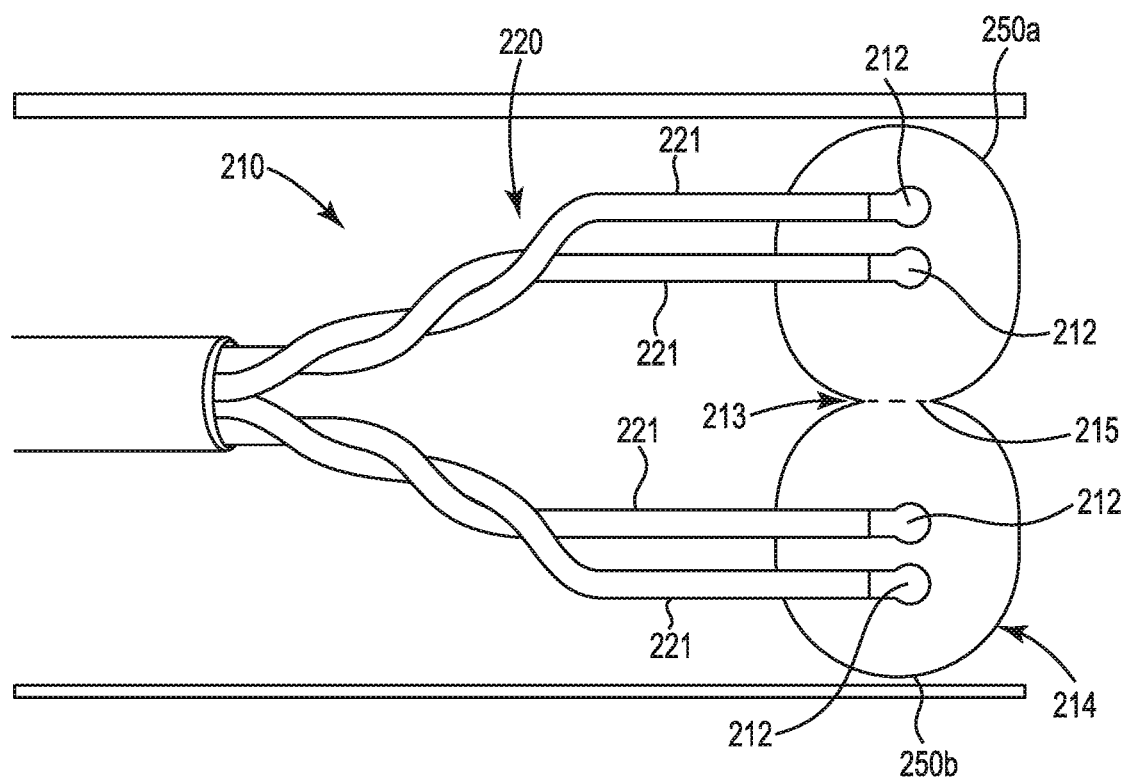
FIG. 12 is a schematic view of an alternate electrode assembly.
Figure 13:
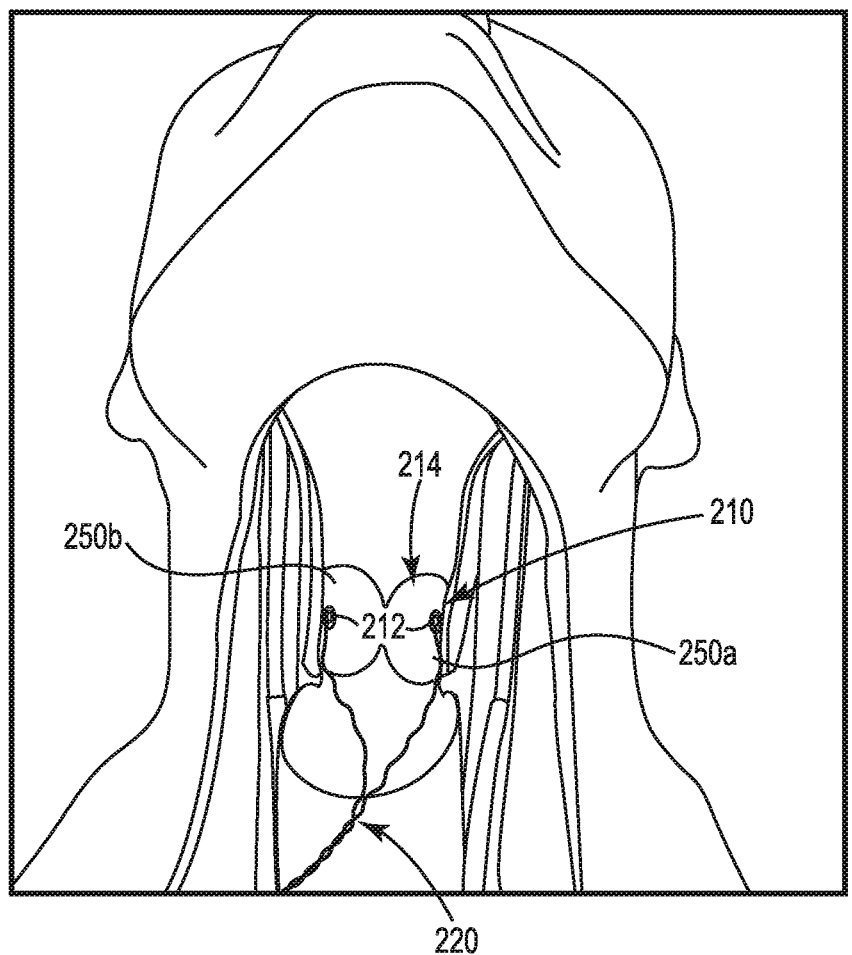
FIG. 13 is a schematic view of the electrode assembly of FIG. 12 operatively secured to thyroid cartilage.

Turning now also to FIGS. 12-13, which illustrate an alternate electrode assembly 210. The electrode assembly 210 includes a plurality (e.g., four) potential monitoring electrodes 212 supported by and positioned within a pledget substrate 214. In example embodiments, each electrode 212 can be supported in the pledget substrate 214 in any manner as disclosed with respect to aforementioned embodiments.

Each electrode 212 can be used as recording and stimulating electrode as well as therapeutic stimulating electrode. Suitable configurations, material examples and properties for each electrode 212 can be similar to those disclosed with respect to electrodes 12 and 112 except as expressly stated. The electrode assembly 210 further includes a lead wire assembly 220 including a lead wire (not visible) at least partially covered by an insulating jacket 222, as disclosed with respect to prior embodiments, for each of the electrodes 212. Except as explicitly stated or illustrated, the lead wire assembly 220 can be configured similar to lead wire assemblies 20, 20', 120 disclosed above.

The pledget substrate 214 includes two bodies 250a, 250b of material interconnected or in contact with one another at a joining region 213. In one embodiment, the joining region 213 has a reduced width or thickness as compared to a maximum width of each of the two bodies 250a, 250b. It could be described that the two bodies 250a, 250b result in an irregular outer boundary of the pledget substrate 214 as a whole. In this way, the bodies 250a, 250b can be cut or otherwise separated at the joining region 213. In one example embodiment, the two bodies 250a, 250b are each round or oblong and have identical proportions. By providing the option to separate the two bodies 250a, 250b, the two bodies 250a, 2850b can be moved or prepositioned with respect to one another. This design is particularly beneficial in obtaining consistent laryngeal EMG data. In many situations, contact between an EMG ET tube surface tube electrodes and the larynx is constantly changing during the course of a procedure thereby forcing the surgeon to manipulate the EMG ET tube every time there is a doubt to rule out a false negative result. Conversely, with the electrode assembly 210, the electrode assembly 210 affixes to thyroid cartilage T as shown in FIG. 13, moves with the larynx and identifies laryngeal EMG twitches. It will be understood that any of the disclosed electrode assemblies can be secured to tissue in a similar manner as illustrated in FIGS. 11 and 13, for example. In one embodiment, the joining region 213 includes perforations 215 to assist in optionally separating the two bodies 250a, 250b. As with prior disclosed embodiments, the pledget substrate 214 affixes to patient tissue from surface tension via Van der Waals forces or bio adhesion such as tissue clotting, drying or scar tissue healing, for example, and is configured to maintain fixation to a nerve or tissue under wet conditions. The electrodes 212 and pledget substrate 214 can be identically configured and function in ways identical to other disclosed embodiments except as explicitly stated. For example, electrodes 212 can be supported within the pledget substrate 214 in any way described herein.

Figure 7A:
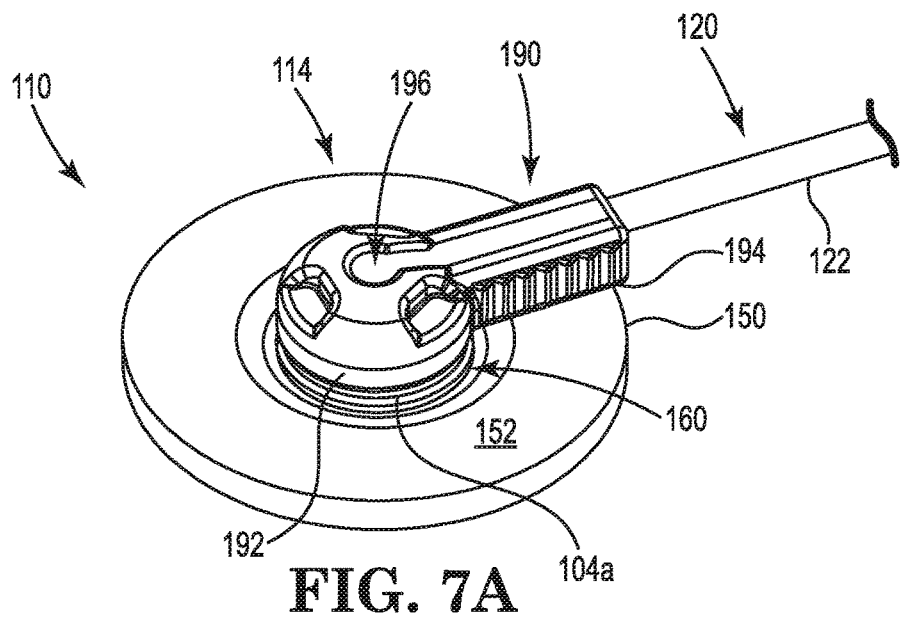
FIG. 7A is a top perspective view of an alternate electrode assembly.
Figure 7B:
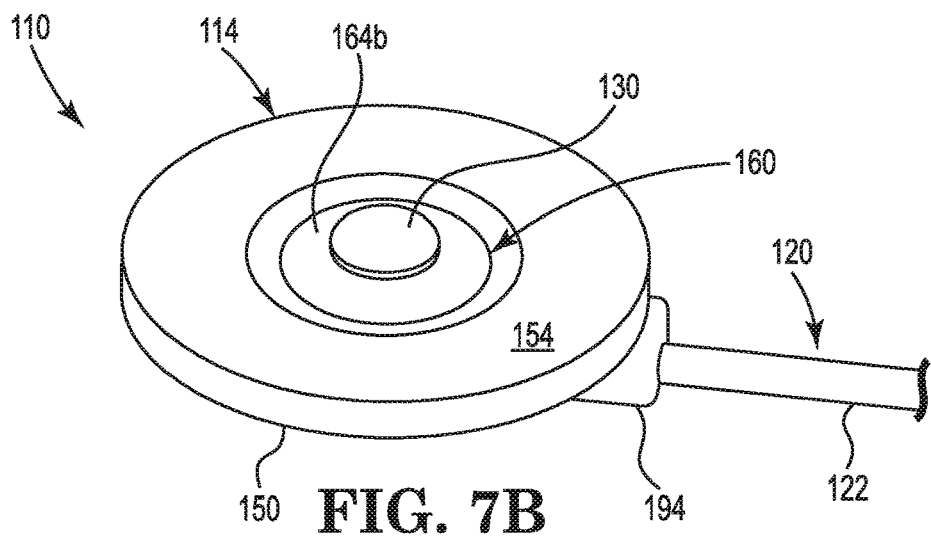
FIG. 7B is a bottom perspective view of the electrode assembly of FIG. 7A.
Figure 7C:
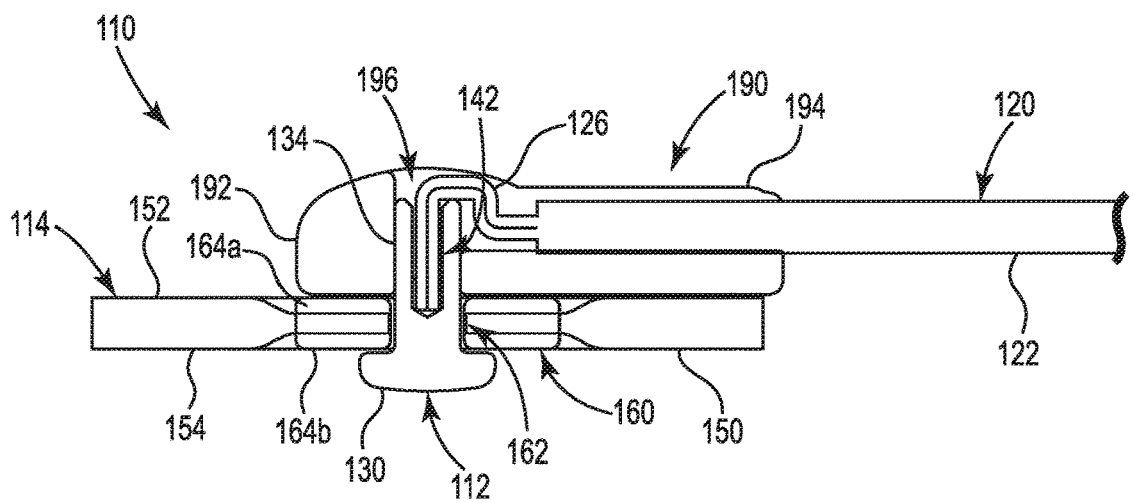
FIG. 7C is cross-sectional view of the electrode assembly of FIG. 7A.
Figure 8:
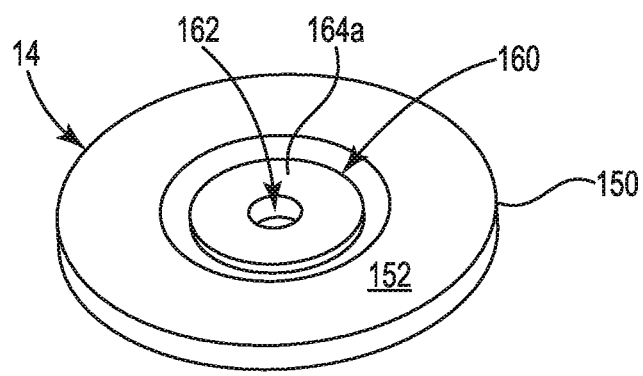
FIG. 8 is a perspective view of a base material and hub of the electrode assembly of FIGS. 7A-7C.
Figure 9:
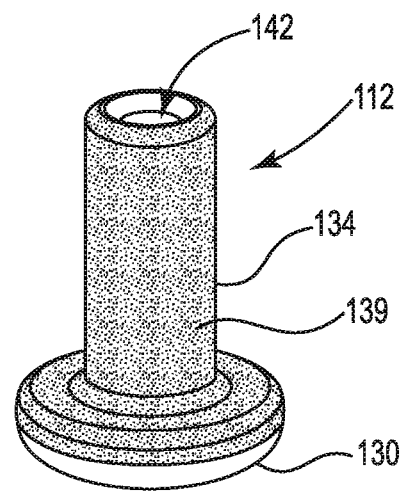
FIG. 9 is a perspective view of an electrode of the electrode assembly of FIGS. 7A-7C.
Figure 10:
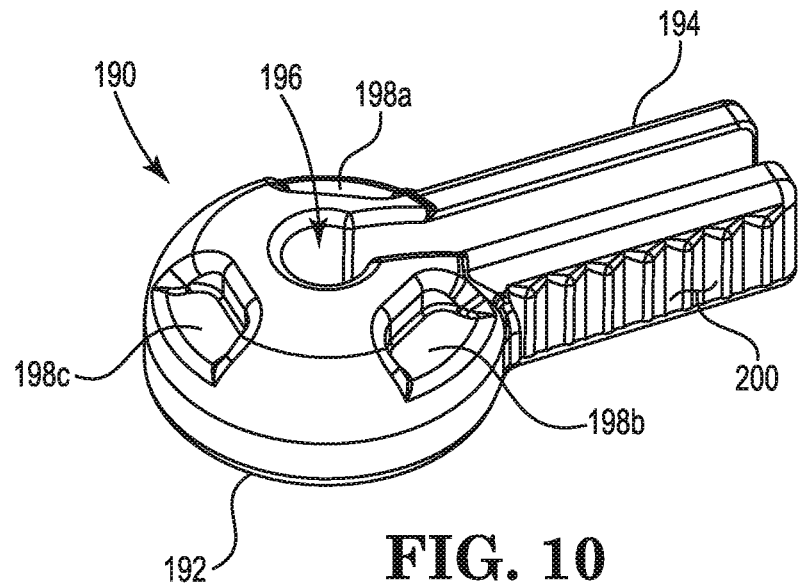
FIG. 10 is a perspective view of a cup of the electrode assembly of FIGS. 7A-7C.

In one experiment, the electrode assemblies of FIGS. 1A and 7A were comparatively tested. To test, each pledget substrate was dunked in saline and operatively placed on a vagus nerve. Stimulation was set at 1 mA with an EMG response of ~1100 μV on both electrode assemblies when the surgical field was "dry". When 2-3 drops from a syringe of saline were placed directly on the respective pledget substrates, they both experienced a decreased EMG response (approximately 50% on the electrode assembly of FIG. 1A and approximately 30% on the electrode assembly of FIG. 7A), however, the electrode assembly of FIG. 7A recovered quickly where the electrode assembly of FIG. 1A did not recover until the surgical field was dried.

Figure 14:
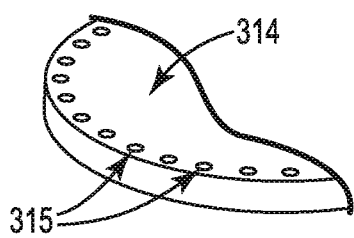
FIG. 14 is a partial, schematic illustration of a pledget substrate including apertures in which sutures and/or staples can be inserted to secure the pledget substrate to a tissue.
Figure 15:
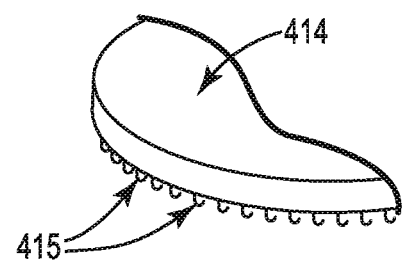
FIG. 15 is a partial, schematic illustration of a pledget substrate including micro hooks to secure the pledget substrate to tissue.
Figure 16:
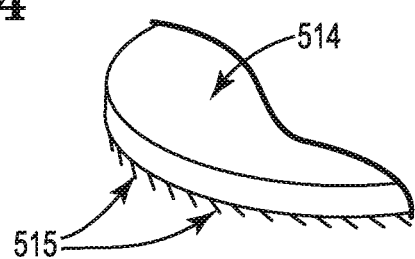
FIG. 16 is a partial, schematic illustration of a pledget substrate including micro needles to secure the pledget substrate to tissue.

Any of the pledget substrates of the present disclosure can optionally be secured to a nerve or other tissue in a variety of manners. A few example methods, which can be utilized individually or in combination, are illustrated in FIGS. 14-16. As illustrated in FIG. 14, the pledget substrate 314 can be secured to tissue with stitches or staples (not shown). In this embodiment, apertures 315 (generally referenced) can be provided in the pledget substrate 314 for the surgeon to thread standard suture or staples therethrough to secure the respective electrode assembly to the tissue via sutures and/or staples.

Turning now also to FIG. 15, which illustrates a pledget substrate 414 that includes micro-hooks 415 (generally referenced) for securing the electrode assembly to tissue. Each of the hooks 415 are semi-rigid (similar to hook fasteners used in hook and loop fastening systems) so that as the hooks 415 are pressed into tissue, they engage the tissue and for removal, the flexibility of each hook 415 naturally straightens after outward pulling forces are applied so that each hook 415 can be pulled free from the tissue.

Turning now also to FIG. 16, which illustrates a pledget substrate 514 that includes micro needles 515 (generally referenced) to assist in securing the pledget substrate 514 to tissue. Micro needles 515 reduce the impedance of the tissue interface and can also be used on the surface of the skin. The micro needles, if provided in an array configuration (generally represented by reference numeral 515), can provide the path for stimulation as well as improve adhesion of the pledget substrate 514 to the tissue. In such embodiments, the micro needles 515 can be straight (perpendicular) or angled (not perpendicular) with respect to a plane defined by the pledget substrate 514, as desired.

As indicated previously, various pledget material substrates were tested to evaluate desirable characteristics including tissue adhesion, ability to remove from tissue, abrasion/roughness (both when dry and wet), pliability and conformability, wettability, lateral stress deformation and post shearing integrity. Each sample tested was a circular swatch of material having a diameter of 0.250 inches.

To test adhesion, a suture was threaded in the center of each pledget substrate sample. The pledget substrate sample was fully saturated with 0.9% saline and placed on a stainless steel sheet. The pledget substrate sample was pull tested in a direction normal to the planar surface of the stainless steel sheet. The adhesion ratings were assigned as indicated in Table 1 below and the results of each test are presented in Tables 5-14.

TABLE 1

Adhesion Ratings

More than 1200 mg = Very Good
1001 mg to 1200 mg = Good
801 mg to 1000 mg = Acceptable
601 mg to 800 mg = Poor
Less than 600 mg = Very Poor To test each substrate material's ability to remove or peel from tissue each pledget substrate sample was threaded with a suture near an edge of the pledget substrate sample. The pledget substrate sample was fully saturated with 0.9% saline and placed on a stainless steel sheet. The pledget substrate sample was pull tested at a 45 degree angle to the planar surface of the stainless steel sheet in the direction of the a central axis of the pledget substrate sample. The peel ratings were assigned as indicated in Table 2 below and the results of each test are presented in Tables 5-14.

TABLE 2

Peel Ratings

More than 300 mg = Very Good
251 mg to 300 mg = Good
201 mg to 250 mg = Acceptable
151 mg to 200 mg = Poor
Less than 150 mg = Very Poor To test each substrate materials' abrasion or roughness both dry and wet, samples of each substrate material were qualitatively evaluated by hand. To score each material, the Likert Scale Qualitative Quality Ratings were used as detailed in Table 3 below.

TABLE 3

Likert Scale Qualitative Quality Ratings

Very Good
Good
Acceptable
Poor
Very Poor

To test each substrate material's pliability/conformability, a 2 mm steel gauge pin was placed on a stainless steel surface. A pledget substrate sample fully saturated with 0.9% saline was draped over the pin and pressed using gloved fingers to conform the pledget substrate sample to the pin geometry. The force was removed and the pledget substrate samples were evaluated based on how well the pledget substrate remained conformed to the pin and stainless steel surface 30 seconds after force removal. To score each material, the Likert Scale Qualitative Quality Ratings were used as detailed in Table 3 above.

To test wettability of each pledget substrate material, a drop of water was applied to the surface of a pledget substrate sample. The substrate sample was observed to see if it was: A) Hydrophilic (absorbs saline well); B) Medium (absorbs saline fairly well with some delay); or C) Hydrophobic (saline drop will sit on surface). The wettability ratings were assigned as summarized in Table 4 below.

TABLE 4

Wettability Ratings

Very Good = Hydrophilic (absorbs saline well)
Acceptable = Medium (absorbs saline fairly well with some delay)
Very Poor = Hydrophobic (saline drop will sit on surface)

To test lateral stress deformation of each pledget substrate sample, samples were "stretched" laterally and evaluated based on materials willingness to plastically deform along any axis. To score each material, the Likert Scale Qualitative Quality Ratings were used as detailed in Table 3 above.

To test post shearing integrity of each pledget substrate sample, each pledget substrate sample was sheared using surgical scissors and ranked qualitatively based on the integrity of the edge (i.e. did the sample exhibit a clean edge?, were there fibers extending beyond the cut line?, etc.) Shearing was performed on a dry pledget substrate sample. To score each material, the Likert Scale Qualitative Quality Ratings were used as detailed in Table 3 above.

As can be seen by the results presented in Tables 5-14 below, the pledget substrate sample made of a 70% Rayon/30% PET blend performed superior overall as compared to other tested samples. The sample made of a 50% Rayon/50% PET blend also performed quite well overall as compared to the other samples.

TABLE 5

| A - Sample Composition | Technology | Basis Weight, g/m2 | Thickness, mm |
|---|---|---|---|
| 100% Rayon | Resin-bond | 31.1 | 0.28 |

Evaluation:

| Test | Rating | Weighting | Weighted Score | Quantitative Value (mg) | Comments |
|---|---|---|---|---|---|
| Adhesion | Poor | 0.86 | 0.9 | 750 | |
| Peel | Acceptable | 0.86 | 1.7 | 250 | |
| Abrasion/Roughness (Dry) | Very Poor | 0.10 | 0.0 | N/A | Feels like a clothes dryer sheet |
| Abrasion/Roughness (Wet) | Poor | 0.40 | 0.4 | N/A | |
| Pliability/conformability | Poor | 0.86 | 0.9 | N/A | Conforms better in preferred orientation - anisotropic Thinnest Material tested |
| Wettability | Very Good | 1.00 | 4.0 | | Wettability Rating: Hydrophilic (absorbs saline well) |
| Lateral stress deformation | Very Good | 0.29 | 1.2 | | |
| Post shearing integrity | Very Good | 0.27 | 1.1 | N/A | |
| Overall Score (0 to 4): | 2.13 | | 2.17 | | |

TABLE 6

| B - Sample Composition | Technology | Basis Weight, g/m2 | Thickness, mm |
|---|---|---|---|
| 100% Rayon | Spunlace | 53 | 0.37 |

Evaluation:

| Test | Rating | Weighting | Weighted Score | Quantitative Value (mg) | Comments |
|---|---|---|---|---|---|
| Adhesion | Acceptable | 0.86 | 1.7 | 1000 | |
| Peel | Good | 0.86 | 2.6 | 300 | Clings well to surface |
| Abrasion/Roughness (Dry) | Very Good | 0.10 | 0.4 | N/A | |
| Abrasion/Roughness (Wet) | Very Good | 0.40 | 1.6 | N/A | |
| Pliability/conformability | Very Good | 0.86 | 3.4 | N/A | Conforms well in all orientations - Isotropic |
| Wettability | Very Good | 1.00 | 4.0 | | Wettability Rating: Hydrophilic (absorbs saline well) |
| Lateral stress deformation | Very Poor | 0.29 | 0.0 | | Easily deforms, risk that it may come free of final device. |
| Post shearing integrity | Acceptable | 0.27 | 0.5 | N/A | |
| Overall Score (0 to 4): | 2.88 | | 3.08 | | |

TABLE 7

| C - Sample Composition | Technology | Basis Weight, g/m2 | Thickness, mm |
|---|---|---|---|
| 65% Rayon/ 35% PET | Spunlace | 50 | 0.35 |

Evaluation:

| Test | Rating | Weighting | Weighted Score | Quantitative Value (mg) | Comments |
|---|---|---|---|---|---|
| Adhesion | Very Good | 0.86 | 3.4 | 1250 | |
| Peel | Good | 0.86 | 2.6 | 300 | |
| Abrasion/Roughness (Dry) | Very Good | 0.10 | 0.4 | N/A | |
| Abrasion/Roughness (Wet) | Very Good | 0.40 | 1.6 | N/A | |
| Pliability/ conformability | Good | 0.86 | 2.6 | N/A | Conforms better in preferred orientation - anisotropic |
| Wettability | Very Good | 1.00 | 4.0 | | Wettability Rating: Hydrophilic (absorbs saline well) |
| Lateral stress deformation | Poor | 0.29 | 0.3 | | |
| Post shearing integrity | Poor | 0.27 | 0.3 | N/A | |
| Overall Score (0 to 4): | 3.00 | | 3.27 | | |

TABLE 8

| D - Sample Composition | Technology | Basis Weight, g/m2 | Thickness, mm |
|---|---|---|---|
| 80% PET/ 20% Viscose | Spunlace | 35 | 0.32 |

Evaluation:

| Test | Rating | Weighting | Weighted Score | Quantitative Value (mg) | Comments |
|---|---|---|---|---|---|
| Adhesion | Good | 0.86 | 2.6 | 1100 | |
| Peel | Acceptable | 0.86 | 1.7 | 250 | Very hydrophobic! Can leave a droplet sitting on sample. - relates to strength? |
| Abrasion/Roughness (Dry) | Good | 0.10 | 0.3 | N/A | |
| Abrasion/Roughness (Wet) | Very Good | 0.40 | 1.6 | N/A | |
| Pliability/ conformability | Poor | 0.86 | 0.9 | N/A | Conforms better in preferred orientation - anisotropic |
| Wettability | Very Poor | 1.00 | 0.0 | | Wettability Rating: Hydrophobic (saline drop will sit on surface) |
| Lateral stress deformation | Acceptable | 0.29 | 0.6 | | |
| Post shearing integrity | Poor | 0.27 | 0.3 | N/A | |
| Overall Score (0 to 4): | 2.00 | | 1.71 | | |

TABLE 9

| E - Sample Composition | Technology | Basis Weight, g/m2 | Thickness, mm |
|---|---|---|---|
| 50% Rayon/ 50% PET | Spunlace | 50 | 0.35 |

Evaluation:

| Test | Rating | Weighting | Weighted Score | Quantitative Value (mg) | Comments |
|---|---|---|---|---|---|
| Adhesion | Very Good | 0.86 | 3.4 | 1250 | |
| Peel | Very Good | 0.86 | 3.4 | 325 | Good peel strength - Sticks better in preferred orientation - anisotropic |
| Abrasion/Roughness (Dry) | Very Good | 0.10 | 0.4 | N/A | |
| Abrasion/Roughness (Wet) | Very Good | 0.40 | 1.6 | N/A | |
| Pliability/conformability | Good | 0.86 | 2.6 | N/A | |
| Wettability | Acceptable | 1.00 | 2.0 | | Wettability Rating: Medium (absorbs saline fairly well with some delay) |
| Lateral stress deformation | Good | 0.29 | 0.9 | | |
| Post shearing integrity | Poor | 0.27 | 0.3 | N/A | |
| Overall Score (0 to 4): | 3.13 | | 3.15 | | |

TABLE 10

| F - Sample Composition | Technology | Basis Weight, g/m2 | Thickness, mm |
|---|---|---|---|
| American Surgical Delicot ® Product Reference Number 63-08 | Spunlace | 63 | 0.33 |

Evaluation:

| Test | Rating | Weighting | Weighted Score | Quantitative Value (mg) | Comments |
|---|---|---|---|---|---|
| Adhesion | Very Good | 0.86 | 3.4 | 1250 | |
| Peel | Very Good | 0.86 | 3.4 | 400 | Dry material exibits some level of being hydrophobic - relates to strength? |
| Abrasion/Roughness (Dry) | Very Good | 0.10 | 0.4 | N/A | |
| Abrasion/Roughness (Wet) | Very Good | 0.40 | 1.6 | N/A | |
| Pliability/conformability | Acceptable | 0.86 | 1.7 | N/A | Conforms better in preferred orientation - anisotropic |
| Wettability | Acceptable | 1.00 | 2.0 | | Wettability Rating: Medium (absorbs saline fairly well with some delay) |
| Lateral stress deformation | Good | 0.29 | 0.9 | | |
| Post shearing integrity | Poor | 0.27 | 0.3 | N/A | |
| Overall Score (0 to 4): | 3.00 | | 2.96 | | |

TABLE 11

| G - Sample Composition | Technology | Basis Weight, g/m2 | Thickness, mm |
|---|---|---|---|
| 100% polypropylene | Spunbound | 36 | approx. 0.33 |

Evaluation:

| Test | Rating | Weighting | Weighted Score | Quantitative Value (mg) | Comments |
|---|---|---|---|---|---|
| Adhesion | Acceptable | 0.86 | 1.7 | 900 | This sample is hard to wet and loses water and therefore adhesion easily |
| Peel | Acceptable | 0.86 | 1.7 | 250 | This sample is hard to wet and loses water and therefore adhesion easily |
| Abrasion/Roughness (Dry) | Good | 0.10 | 0.3 | N/A | |
| Abrasion/Roughness (Wet) | Very Good | 0.40 | 1.6 | N/A | |
| Pliability/conformability | Very Poor | 0.86 | 0.0 | N/A | |
| Wettability | Very Poor | 1.00 | 0.0 | | Wettability Rating: Hydrophobic (saline drop will sit on surface) |
| Lateral stress deformation | Very Good | 0.29 | 1.2 | | |
| Post shearing integrity | Good | 0.27 | 0.8 | N/A | |
| Overall Score (0 to 4): | | 2.25 | 1.58 | | |

TABLE 12

| H - Sample Composition | Technology | Basis Weight, g/m2 | Thickness, mm |
|---|---|---|---|
| 100% polypropylene | Spunbound | 40 | approx. 0.33 |

Evaluation:

| Test | Rating | Weighting | Weighted Score | Quantitative Value (mg) | Comments |
|---|---|---|---|---|---|
| Adhesion | Poor | 0.86 | 0.9 | 750 | This sample is hard to wet and loses water and therefore adhesion easily |
| Peel | Acceptable | 0.86 | 1.7 | 250 | This sample is hard to wet and loses water and therefore adhesion easily |
| Abrasion/Roughness (Dry) | Good | 0.10 | 0.3 | N/A | |
| Abrasion/Roughness (Wet) | Very Good | 0.40 | 1.6 | N/A | |
| Pliability/conformability | Very Poor | 0.86 | 0.0 | N/A | |
| Wettability | Very Poor | 1.00 | 0.0 | | Wettability Rating: Hydrophobic (saline drop will sit on surface) |
| Lateral stress deformation | Very Good | 0.29 | 1.2 | | |
| Post shearing integrity | Good | 0.27 | 0.8 | N/A | |
| Overall Score (0 to 4): | | 2.13 | 1.39 | | |

TABLE 13

| I - Sample Composition | Technology | Basis Weight, g/m2 | Thickness, mm |
|---|---|---|---|
| 100% polypropylene | Spunbound | 45 | approx. 0.33 |

Evaluation:

| Test | Rating | Weighting | Weighted Score | Quantitative Value (mg) | Comments |
|---|---|---|---|---|---|
| Adhesion | Poor | 0.86 | 0.9 | 750 | This sample is hard to wet and loses water and therefore adhesion easily |
| Peel | Acceptable | 0.86 | 1.7 | 250 | This sample is hard to wet and loses water and therefore adhesion easily |
| Abrasion/Roughness (Dry) | Good | 0.10 | 0.3 | N/A | |
| Abrasion/Roughness (Wet) | Very Good | 0.40 | 1.6 | N/A | |
| Pliability/conformability | Very Poor | 0.86 | 0.0 | N/A | |
| Wettability | Very Poor | 1.00 | 0.0 | | Wettability Rating: Hydrophobic (saline drop will sit on surface) |
| Lateral stress deformation | Very Good | 0.29 | 1.2 | | |
| Post shearing integrity | Good | 0.27 | 0.8 | N/A | |
| Overall Score (0 to 4): | 2.13 | | 1.39 | | |

TABLE 14

| J - Sample Composition | Technology | Basis Weight, g/m2 | Thickness, mm |
|---|---|---|---|
| 70% Rayon/30% PET | Spunlace | 40 | 0.23 |

Evaluation:

| Test | Rating | Weighting | Weighted Score | Quantitative Value (mg) | Comments |
|---|---|---|---|---|---|
| Adhesion | Very Good | 0.86 | 3.4 | 1250 | |
| Peel | Very Good | 0.86 | 3.4 | 350 | |
| Abrasion/Roughness (Dry) | Very Good | 0.10 | 0.4 | N/A | |
| Abrasion/Roughness (Wet) | Very Good | 0.40 | 1.6 | N/A | |
| Pliability/conformability | Good | 0.86 | 2.6 | N/A | |
| Wettability | Very Good | 1.00 | 4.0 | | Wettability Rating: Hydrophilic (absorbs saline well) |
| Lateral stress deformation | Poor | 0.29 | 0.3 | | |
| Post shearing integrity | Poor | 0.27 | 0.3 | N/A | |
| Overall Score (0 to 4): | 3.13 | | 3.45 | | |

Figure 17:
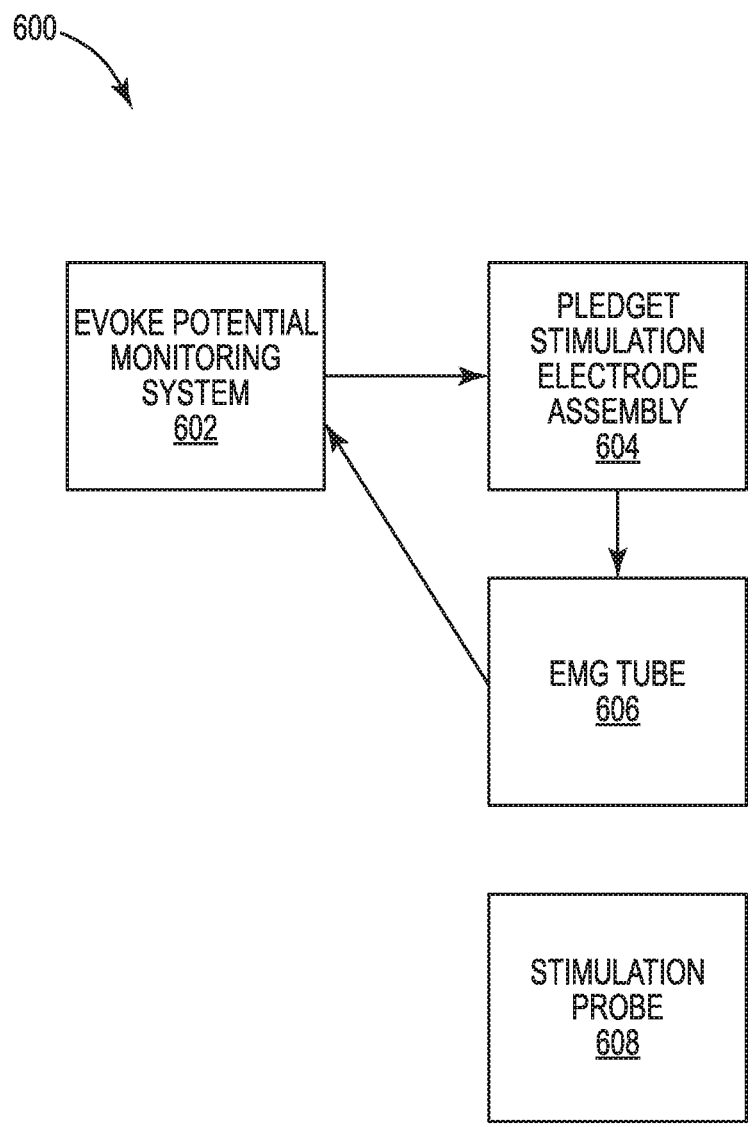
FIGS. 17-19 are a block diagrams of various systems of the disclosure suitable for stimulation and recording during thyroidectomy and neck dissection cancer surgeries.
Figure 18:
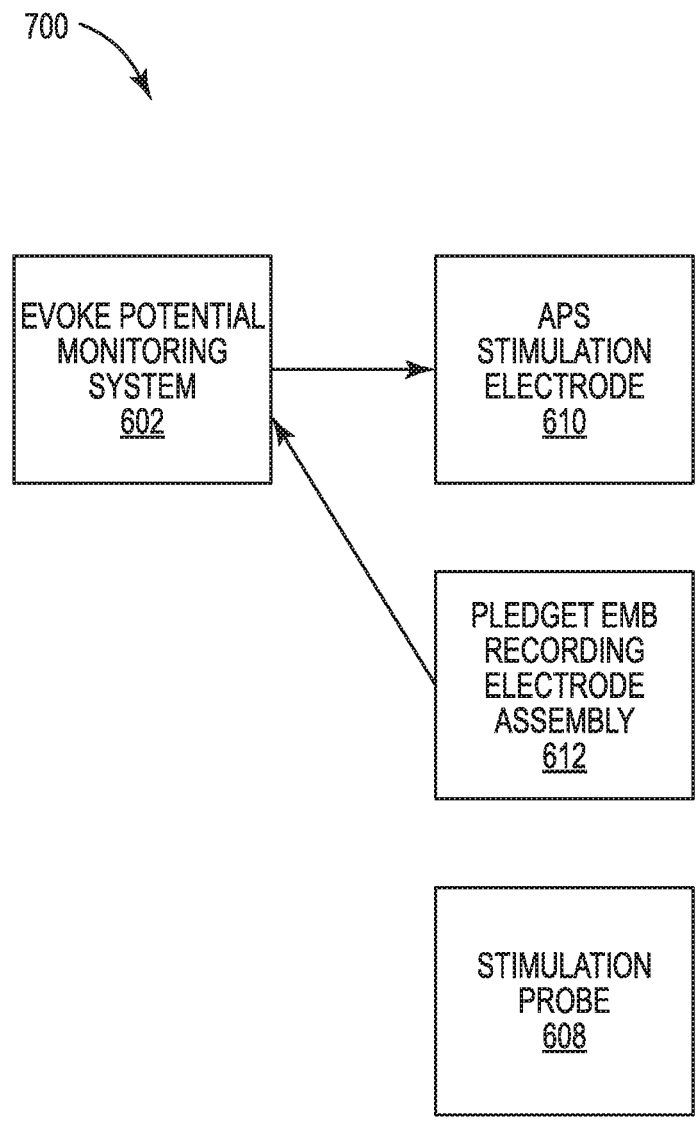
Figure 19:
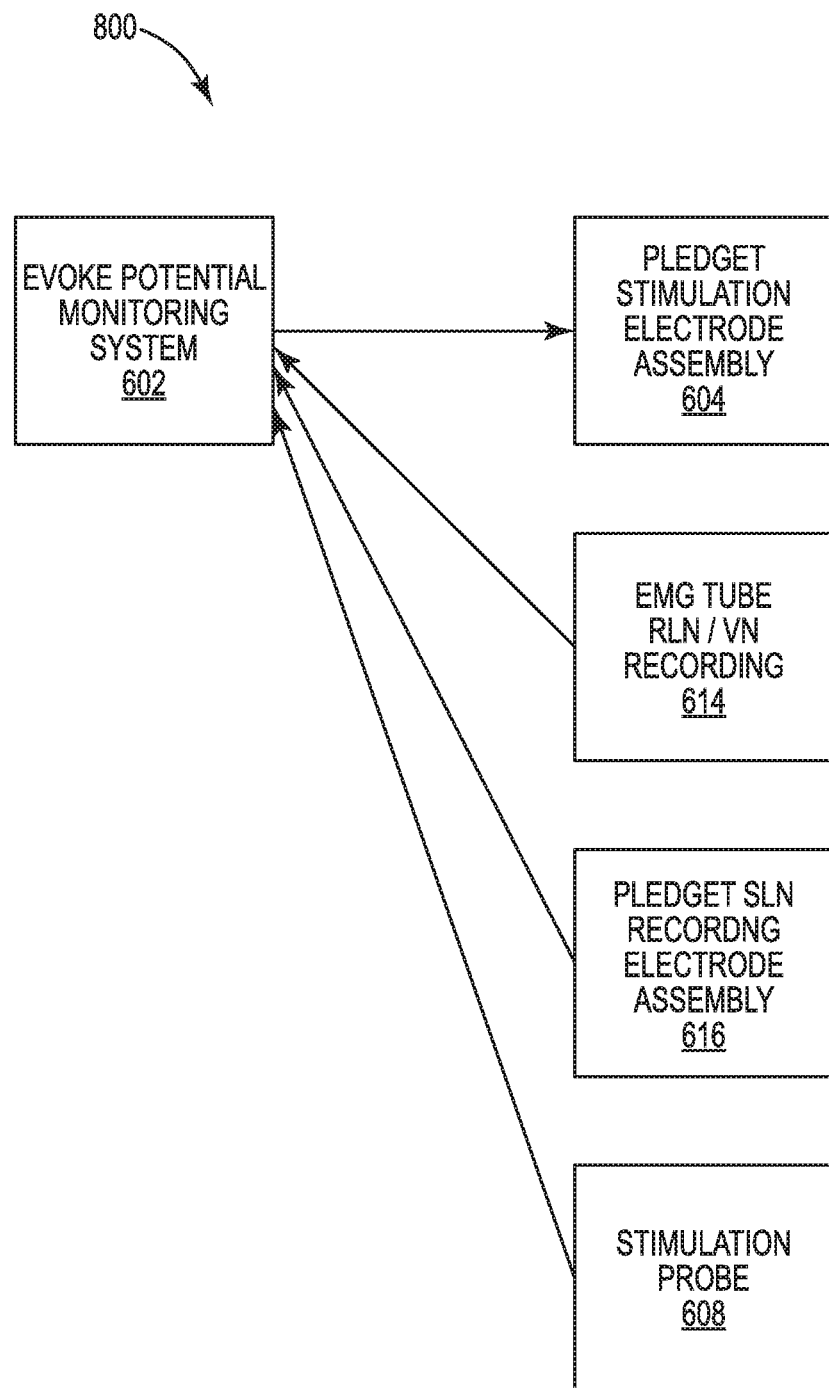

Referring now in addition to FIGS. 17-19, which include block diagrams of various systems 600-800 of the disclosure suitable for stimulation and recording during thyroidectomy and neck dissection cancer surgeries. With the system 600 of FIG. 17, one of the electrode assemblies 604 of the disclosure (e.g., electrode assembly 10, 10', 110) is operatively connected to an evoke potential monitoring system 602, which can be any of the type disclosed herein or known in the art including NIM Eclipse® (Part number 945NCCPUE4), NIM-Response® 3.0 (Part number 8253001) and NIM-Neuro® 3.0 nerve (part number 8253401), referenced above. In addition, the system 600 includes an EMG tube 606. Any known EMG tube is suitable. One example including model number 82-29707, TriVantage® EMG Tube 7 mm, available from Medtronic Xomed, Inc., Jacksonville, Fla. A neural stimulation probe 608 is also provided. Suitable probes 608 include a Standard Prass Flush-Tippart (model number 8225101) or Incrementing Standard Prass Flush tip (model number 82-25825) both available from Medtronic Xomed, Inc., Jacksonville, Fla.

The system 700 of FIG. 18 is similar and includes evoke potential monitoring system 602, one of the electrode assemblies 612 of the disclosure for EMG recording that is operatively connected to evoke monitoring system 602 and also an APS nerve stimulation electrode 610 (e.g., model number 8228052 APS Electrode 2 mm, available from Medtronic Xomed, Inc., Jacksonville, Fla.) operatively connected to evoke potential monitoring system 602. This system also includes stimulation probe 608.

The system 800 of FIG. 19 includes evoke potential monitoring system 602 operatively connected to an electrode assembly of the disclosure 604 for nerve stimulation, EMG tube 614 for recurrent laryngeal nerve and vagus nerve recording, one electrode assembly of the disclosure 616 for superior laryngeal nerve recording and also stimulation probe 608.

Figure 20:
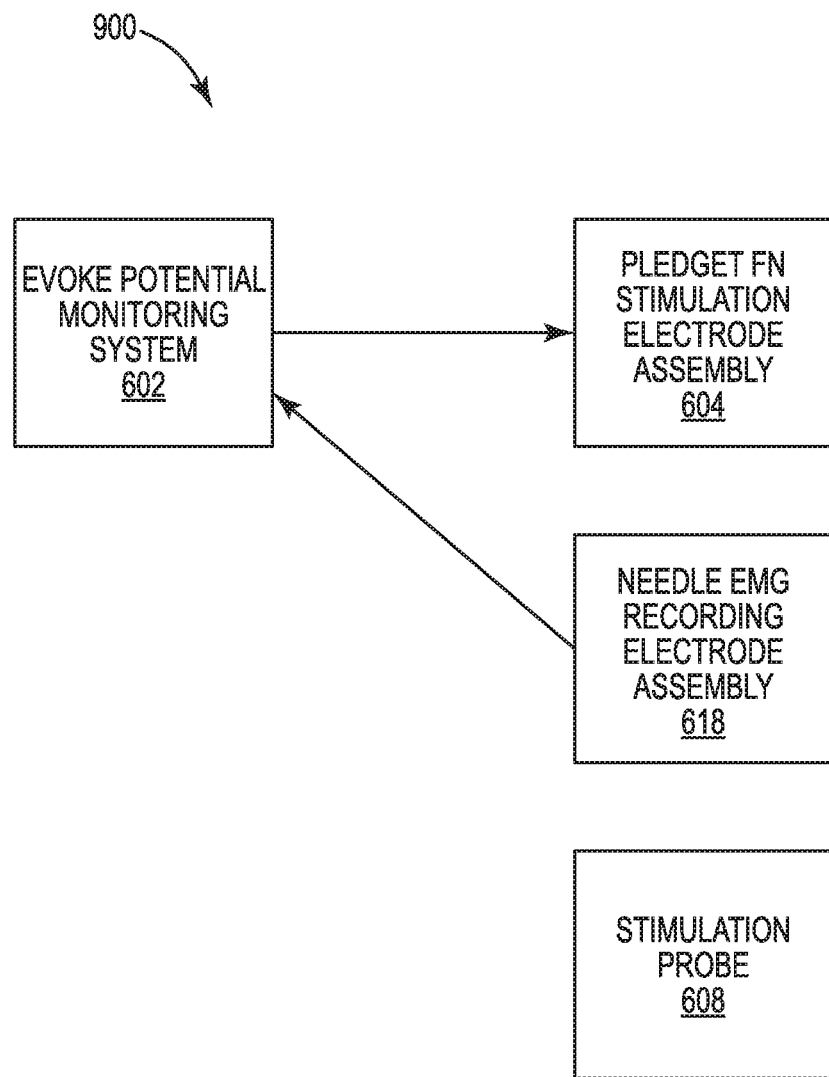
FIG. 20 is a block diagram of a system of the disclosure suitable for parotid surgery or scull base surgery continuous monitoring stimulation of a facial nerve.

FIG. 20 is a block diagram of a system 900 of the disclosure suitable for parotid surgery or scull base surgery continuous monitoring stimulation of a facial nerve. The system 900 includes evoke potential monitoring system 602 operatively connected to one electrode assembly of the disclosure 604 provided for stimulation of a facial nerve and a needle EMG recording electrode 618. One example of a suitable needle EMG recording electrode is model number 82-27411 Paired Subdermal Electrodes 4-CH, available from Medtronic Xomed, Inc., Jacksonville, Fla. In addition the system 900 includes the stimulation probe 608.

Figure 21:
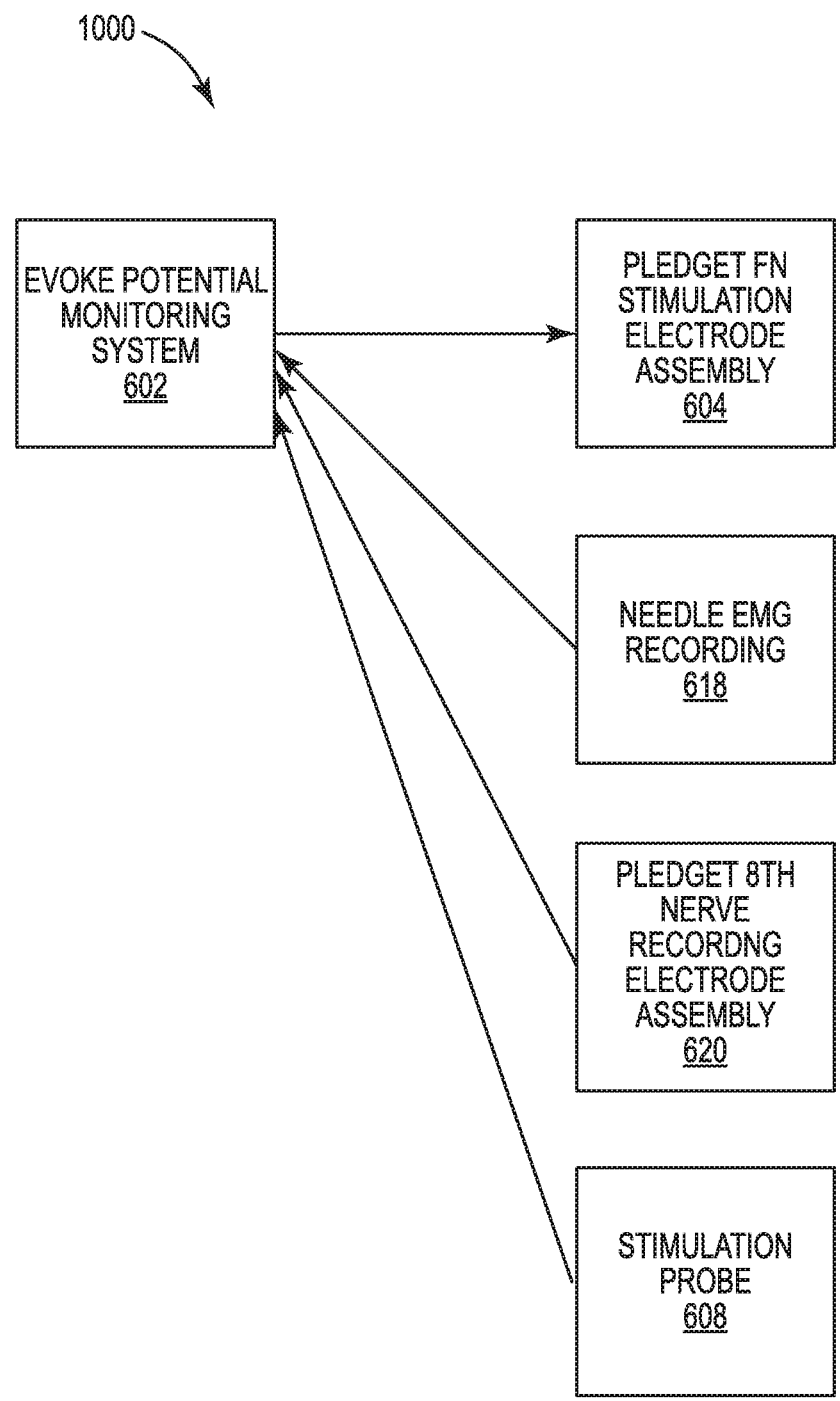
FIG. 21 is a block diagram of a system of the disclosure suitable for scull base surgery with an electrode assembly for continuous monitoring stimulation of a facial nerve and an electrode assembly for direct nerve monitoring of an $8^{th}$ cranial nerve.

FIG. 21 is a block diagram of a system 1000 of the disclosure suitable for scull base surgery with an electrode assembly for continuous monitoring stimulation of a facial nerve and an electrode assembly of the disclosure for direct nerve monitoring of an 8th cranial nerve. The system 1000 includes evoke potential monitoring system 602 operatively connected to one electrode assembly of the disclosure 604 for attachment to and stimulation of a facial nerve. In addition, the evoke potential monitoring system 602 is connected to a needle EMG recording electrode 618. Additionally connected to evoke potential monitoring system 602 is one electrode assembly of the disclosure 620 for attaching to and recording bioelectric responses from an $8^{th}$ cranial nerve. Stimulation probe 608 is also connected to evoke potential monitoring system.

Electrode assemblies disclosed herein can be used in a method of evoked potential monitoring used intraoperatively for nerve stimulation or biopotential recording throughout the body including cranial and peripheral and mixed motor nerves, for example. As indicated above, particularly with respect to FIGS. 17-21, it is envisioned that electrode assemblies of the disclosure can be used exclusively to replace or conjunction with standard electrodes, needle electrodes, continuous monitoring electrodes or with EMG tubes as a complementary method to apply evoked potential monitoring.

Electrode assemblies of the disclosure can be used for evoked potential monitoring throughout the body including cranial and peripheral more or sensory or mixed motor-sensory nerves during surgery, including cerebral cortex, spinal cord, and spinal nerve roots. The electrode assemblies of the disclosure can be used for stimulation, biopotential recording, therapeutic stimulation and automatic periodic stimulation (APS) continuous monitoring of nerves during evoked potential monitoring procedures including, but not limited to: intracranial, extracranial, intratemporal, extratemporal, neck dissections, thoracic surgeries, and upper and lower extremities, degenerative treatments, cortical mapping, pedicle screw procedures, fusion cages, rhizotomy, orthopedic surgery, open and percutaneous lumbar and cervical surgical procedures, and thoracic surgical procedures.

As indicated above, use of the disclosed electrode assemblies for evoked potential monitoring methods can replace or supplant current methods. For example, during thyroidectomy procedures nerve monitoring is used to preserve and protect the nerves of the larynx (recurrent laryngeal nerve, superior laryngeal nerve, vagus nerve). Evoked potential monitoring (stimulating and recording) is typically accomplished by stimulating the nerve with a hand-held stimulator probe for locating and assessing neural function. Continuous monitoring stimulation of the vagus nerve is accomplished by use of Automatic Periodic Stimulation (APS). Recording the EMG responses is typically conducted by recording EMG from innervated muscle with an EMG tube (endorectal tube with integrated recording electrodes) or invasive needle electrodes placed in the muscles of the larynx percutaneously or intraorally. The present inventors have discovered current methods have shortcomings. The APS electrodes need to place circumferentially around the stimulated nerve which invasive and presents risk for neurological damage without careful dissection surgical skill. EMG tubes are specialty electrodes are complex and expensive. Both conventional devices are dependent on operator placement to be effective and time consuming to reposition.

Methods of the disclosure for evoked potential monitoring (stimulation and/or recording) with electrode assemblies of the disclosure simplify device, placement positioning, and replacement if needed for improving the cost effectiveness and product application ease-of-use. The electrode assemblies of the disclosure can be replace an APS electrode in known systems (FIGS. 17 and 19). The electrode assemblies of the disclosure can be wetted and placed on the nerve as compared to a known APS electrode that requires 360 degree dissection of the nerve the electrode will be applied to. The electrode assemblies of the disclosure can be used throughout the body. For example, the electrodes assemblies can be used to stimulate the vagus nerve during continuous monitoring during thyroid and neck dissection procedures. Electrode assemblies of the disclosure can also be used for stimulation during continuous monitoring of the facial nerves during parotid or skull base procedures (FIGS. 20-21).

It is envisioned that the electrode assemblies of the disclosure can also replace use of an EMG tube (FIG. 18). The new electrode assemblies of the disclosure can be wetted and placed latterly on the exposed trachea as compared to an EMG tube electrode, which must be placed at intubation and positioned carefully to record proper EMG responses. Also, the EMG tube can be displaced during surgery which is difficult to visualize and remedy as it is also maintaining the patient airway during the operation. The pledget substrate placement is visually apparent and easily replaced or moved during the thyroid surgery. A twisted pair pledget substrate can be positioned with one electrode on each side of the trachea for single channel referential EMG recording or a pair can be placed on each side of the trachea for two channel side specific recording.

It is further envisioned that electrode assemblies of the disclosure can be placed directly on the cricothyroid muscle for recording specific superior laryngeal nerve responses as compared to needle electrodes, which are invasive and can damage the delicate musculature.

For example, the electrode assemblies of the disclosure can record 8th cranial nerve evoked response or provide continuous stimulation of the facial nerve intracranially (FIG. 21). Methods of using the electrode assemblies of the disclosure are easier and less evasive to place on delicate intracranial nerves. The electrode assemblies of the disclosure can be replace the use of a Cueva C-shaped electrode for cranial stimulation or recording nerve. The electrode assemblies of the disclosure can be wetted and placed on the nerve with minimal manipulation as compared to placing the Cueva C-shaped electrode around the nerve requires that the delicate intracranial nerve be dissected to accept the Cueva electrode.

One method of conducting an intraoperative nerve monitoring and/or stimulation procedure using the systems 600-1000 can generally be conducted as follows. Electrode assemblies 10, 10', 10", 110, 210 of the present disclosure can optionally be delivered through a cannula inserted within a skin incision to access bioelectric tissue of a patient. The tissue can be a nerve, such as a recurrent laryngeal nerve, a superior laryngeal nerve, a vagus nerve, peripheral or a cranial nerve. In other embodiments, the tissue can be a trachea. In additional embodiments, the tissue can be innervated muscle or cricothyroid muscle. In some embodiments, the cannula and skin incision are equal to or greater than 2.5 mm. Once the desired tissue is accessed, the pledget substrate is applied to the tissue. Therefore, no dissection of the nerve or tissue on which the pledget substrate is secured is required. Such application can include optionally wetting the pledget substrate with saline and then wrapping the pledget substrate around the tissue. In embodiments where micro hooks or micro needles are provided on the pledget substrate, they may be applied to be inserted within the tissue. If apertures are provided in the pledget substrate, the pledget substrate can be sewn or stapled into the tissue through the apertures. Due to the hydrophilic nature of the pledget substrate, the pledget substrate will naturally absorb moisture present at the target tissue, which will retain the pledget substrate to the nerve. In some embodiments, the substrate is wrapped around less than an entire circumference (i.e. less than 360 degrees of the circumference) of the tissue. In some embodiments, the pledget substrate is applied to cover less than 360 degrees of the circumference of the tissue but greater than 20 degrees of the circumference of the tissue. Once applied, methods can include recording bioelectric responses of the tissue sensed from one or more electrodes of the electrode assembly. The bioelectric response can include EMG activity or direct nerve recording. In some embodiments the stimulation is therapeutic stimulation applied to the tissue. In methods where the electrode assembly of FIG. 12 utilized, the user can optionally disconnect the first and second bodies of the pledget substrate, either along the perforation or otherwise, as desired, it is to be understood that the system provided in the method includes one evoke potential monitoring system operatively connected to the electrode assembly. The connector of the lead wire assembly can be secured to the evoke potential monitoring system of the type disclosed herein either prior to or after the electrode assembly is positioned on the tissue.

In alternate embodiments, stimulation can be applied to the tissue via the electrode of the electrode assembly of FIG. 7A, the user may optionally adjust the direction of the lead wire assembly via rotating the cup about the pledget substrate.

Although the present disclosure has been described with reference to preferred embodiments, workers skilled in the art will recognize that changes can be made in form and detail without departing from the spirit and scope of the present disclosure. It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. An intraoperative electrode assembly comprising:
 a pledget substrate having a first surface that is hydrophilic;
 a first electrode supported by and positioned within the pledget substrate, the first electrode including a top having first and second channels; and
 a lead wire assembly interconnected to the first electrode; wherein the lead wire assembly is received in the first channel, extends out of the top and then into the second channel;
 wherein the top includes a spherically-shaped domed portion and a conically-shaped flange portion; further wherein the first channel is formed through the spherically-shaped domed portion to define a first bore and the second channel is formed through the conically-shaped flange portion to define a second bore.

2. The electrode assembly of claim 1, wherein the lead wire assembly includes an insulating jacket positioned around a wire core; the first electrode further including an insulating cup interconnecting the first electrode and the insulating jacket.

3. The electrode assembly of claim 2, wherein the insulating cup is configured to rotate about the pledget substrate.

4. The electrode assembly of claim 1, wherein the pledget substrate is a rayon and polyethylene terephthalate blend.

5. The electrode assembly of claim 1, wherein a material of the pledget substrate is a lint free material.

6. The electrode assembly of claim 1, wherein the material is further a porous material.

7. The electrode assembly of claim 1, wherein the first electrode is supported by and positioned within the pledget substrate with at least one spacer that allows for the pledget substrate to rotate about the first electrode.

8. The electrode assembly of claim 1, wherein the pledget substrate includes a coating.

9. The electrode assembly of claim 8, wherein the coating includes a binder, water and surfactant.

10. The electrode assembly of claim 1, further comprising a connector configured to be connected to a nerve monitoring system.

11. The electrode assembly of claim 1, wherein the pledget substrate includes one or more of micro hooks or micro needles.

12. The electrode assembly of claim 11, wherein the pledget substrate includes an array of micro needles.

13. The electrode assembly of claim 1, wherein a first side of the pledget substrate includes a hydrophilic first coating and a second side of the pledget substrate includes a hydrophobic coating.

14. The electrode assembly of claim 1, wherein the first electrode is supported by and positioned within the pledget substrate with at least one spacer.

15. The electrode assembly of claim 14, wherein each spacer includes a retaining structure.

16. The electrode assembly of claim 1, wherein the pledget substrate includes a plurality of perforations.

17. The electrode assembly of claim 1, wherein the first electrode includes a top, a base and an axle interconnecting the top and base.

18. The electrode assembly of claim 1, further comprising a second electrode.

19. The electrode assembly of claim 18, wherein the pledget substrate includes first and second bodies in contact with each other, wherein the first electrode is positioned within the first body and the second electrode is positioned within the second body; further wherein the first and second bodies are configured to be separable.

* * * * *

UNITED STATES PATENT AND TRADEMARK OFFICE
CERTIFICATE OF CORRECTION

PATENT NO. : 11,672,487 B2
APPLICATION NO. : 16/152624
DATED : June 13, 2023
INVENTOR(S) : Matthew L. Cantwell et al.

It is certified that error appears in the above-identified patent and that said Letters Patent is hereby corrected as shown below:

On the Title Page

Page 3, Column 2, Other Publications, Line 22, Delete "Acessory" and insert --Accessory-- therefor In the Specification Column 10, Detailed Description, Line 34, Delete "$2850b$" and insert --$250b$-- therefor Signed and Sealed this
Seventeenth Day of October, 2023

Katherine Kelly Vidal
*Director of the United States Patent and Trademark Office*